(12) United States Patent
Aebi et al.

(10) Patent No.: US 6,444,829 B1
(45) Date of Patent: Sep. 3, 2002

US006444829B1

(54) PYRROLIDINE COMPOUNDS

(75) Inventors: Johannes Aebi, Basel (CH); Henrietta Dehmlow, Grenzach-Wyhlen (DE); Eric Argirios Kitas, Arlesheim (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/900,350

(22) Filed: Jul. 6, 2001

(30) Foreign Application Priority Data

Jul. 19, 2000 (EP) .............................. 00114948

(51) Int. Cl.⁷ ............................................ C07D 207/48
(52) U.S. Cl. ................................................. 548/537
(58) Field of Search ................................ 548/541, 542, 548/556, 537

(56) References Cited

U.S. PATENT DOCUMENTS

| | | | | | |
|---|---|---|---|---|---|
| 4,933,333 | A | * | 6/1990 | Sunagawa et al. | 514/192 |
| 4,943,569 | A | * | 7/1990 | Sunagawa et al. | 514/210 |
| 5,952,369 | A | * | 9/1999 | Ito et al. | 514/424 |

\* cited by examiner

*Primary Examiner*—Floyd D. Higel
*Assistant Examiner*—Golam M. M. Shameem
(74) *Attorney, Agent, or Firm*—George W. Johnston; Robert A. Silverman

(57) ABSTRACT

The present invention relates to a pyrrolidine compound and pharmaceutically acceptable esters and/or salts thereof. The compounds are useful as inhibitors of metalloproteases, e.g. zinc proteases, particularly zinc hydrolases, and which are effective in treating disease states are associated with vasoconstriction of increasing occurrences.

42 Claims, No Drawings

PYRROLIDINE COMPOUNDS

FIELD OF THE INVENTION

The present invention is directed to compounds which are useful as inhibitors of metalloproteases, e.g. zinc proteases, particularly zinc hydrolases, and which are effective in the prophylaxis and treatment of disease states which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid hemorrhage, Raynaud syndrome and pulmonary high pressure. In addition the compounds are useful as cytostatic and cerebroprotective agents for inhibition of graft rejection, for organ protection and for treatment of ophthalmological diseases.

BACKGROUND

Endothelins are peptides, that exist in three isoforms ET-1, ET-2, and ET-3, each encoded by a distinct gene. They have been originally discovered in the conditioned medium of porcine endothelial cells in 1988 by Yanagisawa (Yanagisawa M; Kurihara H; Kimura S; Tomobe Y; Kobayashi M; Mitsui Y; Yazaki Y; Goto K; Masaki T: A novel potent vasoconstrictor peptide produced by vascular endothelial cells [see comments]. NATURE (Mar. 31, 1988), 332(6163), 411–5.). The active ETs are peptides of 21 amino acids with two intramolecular disulfide bridges. They are produced from preproproteins of 203 to 212 amino acids which are processed by furin like endopeptidases to the biologically inactive big-endothelin (big-ET). The big-ETs are specifically processed to mature ETs by a hydrolytic cleavage between amino acids 21 and 22 that are $Trp^{21}$-$Val^{22}$ (big-ET-1, big ET-2) and $Trp^{21}$-$Ile^{22}$ in big-ET-3 respectively. Already in 1988 a specific metalloprotease was postulated to be responsible for this specific cleavage. In 1994 ECE-1 (endothelin converting enzyme-1) was purified and cloned from bovine adrenal (Xu D, Emoto N, Giaid A, Slaughter C, Kaw S, de Witt D, Yanagisawa M: ECE-1: a membrane-bound metalloprotease that catalyzes the proteolytic activation of big endothelin-1. Cell (1994) 78: 473–485.).

ECE-1 is a membrane bound type II zinc-endopeptidase with a neutral pH optimum and a zinc binding motif HExxHx(>20)E. It belongs to subfamily M13 and has a large 681 amino acid ectodomain that comprises the active site. Other members of the M13 family are NEP24.11 (neutral endopeptidase), PEX, a phosphate regulating neutral endopeptidase, and Kell blood group protein that has recently been described as a big-ET-3 processing enzyme. Members of the M13 family of human origin are characterized by a high molecular weight (>80 kDa) a number of conserved disulfide bridges and a complex glycosylation pattern. The structure of NEP has recently been solved. (Oefner et al, J. Mol. Biol. 2000, 296, 341–349). The catalytic domain of ECE and related human M13 proteinases are significantly larger (>650 amino acids) than members of matrix metalloproteases (MMPs). Unlike the family of the MMPs which belong to the metzincins and display a typical HExxHxxGxxH pattern members of the M13 family are gluzincins comprising a HExxHx(>20)E pattern. These two families are clearly different in size of catalytic domains, structure and zinc coordinating pattern of ligands. Active sites of the two families show clear differences which has clear impact on type of inhibitors and the potential selectivity.

Therefore one aspect of the present invention is to provide compounds useful for the selective inhibition of ECE-1.

BRIEF SUMMARY OF THE INVENTION

The present invention relates to a compound of formula (I):

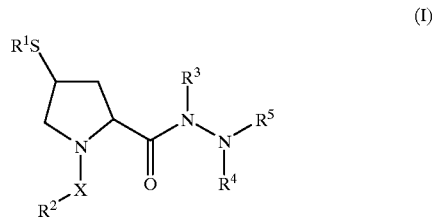

wherein
$R^1$ is hydrogen, alkylcarbonyl, or arylcarbonyl;
$R^2$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or hetercycylalkyl;
$R^3$ is hydrogen, aryl, alkyl, or arylalkyl, arylsulfonyl, heteroarylsulfonyl;
$R^4$ is hydrogen, arylalkyl, alkyl, aryl, cycloalkyl, cycloalkylalkyl, alkylsulfonyl, arylsulfonyl, arylalkylsulfonyl, heteroarylsulfonyl, carboxyalkyl, carboxyalkylsulfonyl, or alkoxycarbonylalkyl; or the groups —$NR^3R^4$ or $R^5$—[N—N($R^4$)]—$R^3$ form a saturated or unsaturated 5- or 6-membered aliphatic ring;
$R^5$ is hydrogen, alkylsulfonyl, arylsulfonyl, heteroarylsulfonyl, alkoxycarbonyl, aryloxycarbonyl, heteroaryloxycarbonyl, alkylcarbonyl, arylcarbonyl, heteroarylcarbonyl, heteroarylalkylcarbonyl, heterocyclyl, (mono- or di-alkylamino)-alkylcarbonyl, (mono- and dialkyl)aminosulfonyl, arylaminocarbonyl, alkyl alkylcarbonyl, alkoxycarbonyl, aryl, arylalkyl, arylalkoxycarbonyl, or heteroaryl;
$R^6$ is hydrogen, alkyl, aryl, or carboxyalkyl;
X is —$S(O)_2$—, —$S(O)_2$—NH—, —C(O)—, —C(O)$NR^6$ or C(O)—O—, or a pharmaceutically acceptable esteror pharmaceutically acceptable salt thereof.

DETAILED DESCRIPTION OF THE INVENTION

The term "alkyl" as used herein, alone or in combination, means a straight-chain or branched-chain alkyl group containing a maximum of 7, preferably a maximum of 4, carbon atoms, e.g., methyl, ethyl, n-propyl, 2-methylpropyl (isobutyl), 1-methylethyl (iso-propyl), n-butyl, and 1,1-dimethylethyl (t-butyl).

The term "carboxy" refers to the group —C(O)OH.

The term "carbamoyl" refers to the group —C(O)$NH_2$.

The term "carbonyl" refers to the group —C(O)—.

The term "halogen" refers to the group "fluoro, bromo, chloro and iodo, preferably fluoro and/or chloro, most preferably fluoro.

The term "sulfonyl" refers to the group —$S(O_2)$—.

The term "alkenyl" refers to a hydrocarbon chain as defined for alkyl having at least one olefinic double bond (including for example, vinyl, allyl and butenyl).

The term "alkinyl" refers to a hydrocarbon chain as defined for alkyl having at least one olefinic triple bond (including for example propinyl, butin-(1)-yl, etc.

The term "alkoxy", alone or in combination, means an alkyl ether group in which the term 'alkyl' has the significance given earlier, such as methoxy, ethoxy, n-propoxy, isopropoxy, n-butoxy, isobutoxy, sec.butoxy, tert.butoxy and the like.

The term "alkoxycarbonyl" refers to refers to a group of the formula —C(O)$R_c$ wherein $R_c$ is alkoxy as defined above.

The term "hydroxy" refers to the group —OH, the term "cyano" to the group —CN.

The term "hydroxyalkyl" means an alkyl group as defined earlier which is substituted by a hydroxy group.

The term "thioalkyl" refers to an alkyl group as defined above which is substituted by a —SH group.

The term "halogenalkyl" refers to an alkyl group as defined earlier which is substituted by one to three halogen atoms, preferably fluoro, e.g. trifluoromethyl, 2,2,2-trifluoroethyl, etc.

"Carboxyalkyl" means a lower-alkyl as defined above which is substituted by a HOOC-group.

The term "alkylcarbonyl", alone or in combination, means an acyl group derived from an alkanecarboxylic acid, i.e. alkyl-C(O)—, such as acetyl, propionyl, butyryl, valeryl, 4-methylvaleryl etc.

The term "cycloalkyl", alone or in combination, signifies a saturated, cyclic hydrocarbon group with 3–8, preferably 3–6 carbon atoms, i.e. cyclopropyl, cyclobutyl, cyclopentyl and cyclohexyl and the like.

The term "amino" refers to the group —$NH_2$.

The term "aryl" for $R^2$— alone or in combination-, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups, preferably 1–5, more preferably 1–3, independently selected from halogen, preferably fluor, alkoxycarbonyl, e.g. methylcarbonyl, carboxy, cyano, alkyl, alkoxy, phenyl, phenoxy, trifluormethyl, trifluormethoxy, more preferably fluor, alkoxycarbonyl, alkyl, trifluoromethyl and trifluoromethoxy and most preferably fluor. The most preferred aromatic groups are naphthyl or phenyl substituted with one or more fluor atoms, e.g. naphthyl, 2,3,4,5,6-pentafluorophenyl or biphenyl.

The term "aryl" for $R^3$ and $R^6$— alone or in combination—refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups, preferably 1–5, more preferably 1–3, independently selected from halogen, preferably fluor, alkoxycarbonyl, e.g. methylcarbonyl, carboxy, cyano, alkyl, alkoxy, phenyl, phenoxy, trifluormethyl, trifluormethoxy, hydroxy, alkylamido, e.g. acetamido, nitro, alkylsulfonyl, e.g. methylsulfonyl, more preferably alkyl or alkoxy.

The term "aryl" for $R^4$— alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups, preferably 1 to 3, independently selected from halogen, preferably fluor, alkoxycarbonyl, e.g. methylcarbonyl, carboxy, cyano, alkyl, alkoxy, phenyl, phenoxy, trifluormethyl, trifluormethoxy, cyclohexyl, hydroxy, alkylamido, e.g. acetamido, nitro, alkylsulfonyl, e.g. methylsulfonyl, more preferably fluor, chlor, brom, alkoxy, carboxy, alkoxycarbonyl, and most preferably fluor. Examples for aromatic groups are phenyl, 2,4,5-trifluorophenyl, and 2,4-difluorophenyl.

The term "aryl" for $R^5$— alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably or phenyl. The aryl moiety is optionally substituted with one or more groups, preferably 1–5, more preferably 1–3, independently selected from halogen, preferably fluor, alkoxycarbonyl, e.g. methylcarbonyl, carboxy, cyano, alkyl, alkoxy, phenyl, phenoxy, trifluormethyl, trifluormethoxy, more preferably alkyl or alkoxy, e.g. methyl or methoxy. Examples for these aryl groups are 4-methyl-phenyl and 4-methoxy-phenyl.

The term "aryloxy" refers to an aryl group as defined above attached to a parent structure via an oxy radical, i.e., aryl-O—.

The term "heteroaryl" for $R^4$— alone or in combination— refers to an aromatic monovalent mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, pyridinyl, pyrrolyl, imidazolyl, tetrazolyl, preferably pyridinyl, isoxazolyl and thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heteroaryl" for $R^3$ or $R^5$— alone or in combination—refers to an aromatic monovalent mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are pyridinyl, thiophenyl, isoxyzolyl, isoquinolyl, quinolyl, indolyl, pyrimidine, pyridazine, and pyrazine, preferably thiophenyl, furanyl, pyrrolidinyl, indolyl and isoxazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, oxo, alkoxycarbonylalkyl, preferably alkyl.

The term "heterocyclyl"—alone or in combination— refers to a non-aromatic monovalent mono- or bicyclic radical having 5 to 10, preferably 5 to 6 ring atoms, containing one to three heteroatoms, preferably one heteroatom, e.g. independently selected from nitrogen, oxygen or sulfur. Optionally the heterocyclic ring can be substituted by a group independently selected from halogen, alkyl, alkoxy, oxocarboxy, alkoxycarbonyl, etc. and/or on a secondary nitrogen atom (i.e. —NH—) by alkyl, arylalkoxycarbonyl, alkylcarbonyl or on a tertiary nitrogen atom (i.e. =N—) by oxido. Examples for heterocyclic groups are morpholinyl, pyrrolidinyl, piperidyl, etc.

The term "dimeric form" means a compound wherein the two $R^1$ groups of two identical compounds of formula I have been replaced by a common single bond or wherein $R^1$ is glutathione-S— or cysteine-S— or ester and/or alkylcarbonyl or arylcarbonyl derivatives thereof, e.g. acetylcysteine-S— or benzoylcysteine-S—, preferably glutathione-S—, cysteine-S—, acetylcysteine-S— or benzoylcysteine-S—.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) and their salts and esters are useful in inhibiting mammalian metalloprotease activity, particularly zinc hydrolase activity. More specifically, the compounds of formula (I) and their salts and esters are useful as medicaments for the treatment and prophylaxis of disorders which are associated with diseases caused by endothelin-converting enzyme (ECE) activity. Inhibiting of this enzyme would be useful for treating myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma. In addition the compounds are useful as cytostatic and cerebroprotective agents, for inhibition of graft rejection, for organ protection and for treatment of ophthalmological diseases.

In more detail, the present invention relates to a compound of formula (I)

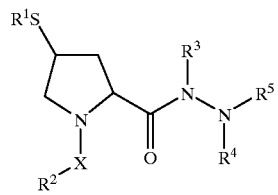

(I)

wherein
$R^1$ is hydrogen, alkylcarbonyl, or arylcarbonyl;
$R^2$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl (alkoxycarbonyl)alkyl, heteroaryl, heteroarylalkyl, heterocyclyl or hetercycylalkyl;
$R^3$ is hydrogen, aryl, alkyl, or arylalkyl, arylsulfonyl, heteroarylsulfonyl;
$R^4$ is hydrogen, arylalkyl, alkyl, aryl, cycloalkyl, cycloalkylalkyl, alkylsulfonyl, arylsulfonyl, arylalkylsulfonyl, heteroarylsulfonyl, carboxyalkyl, carboxyalkylsulfonyl, or alkoxycarbonylalkyl; or the groups —$NR^3R^4$ or $R^5$—[N—N($R^4$)]—$R^3$ form a saturated or unsaturated 5- or 6-membered aliphatic ring;
$R^5$ is hydrogen, alkylsulfonyl, arylsulfonyl, heteroarylsulfonyl, alkoxycarbonyl, aryloxycarbonyl, heteroaryloxycarbonyl, alkylcarbonyl, arylcarbonyl, heteroarylcarbonyl, heteroarylalkylcarbonyl, heterocyclyl, (mono- or di-alkylamino)-alkylcarbonyl, (mono- and dialkyl)aminosulfonyl, arylaminocarbonyl, alkyl, alkylcarbonyl, alkoxycarbonyl, aryl, arylalkyl, arylalkoxycarbonyl, or heteroaryl;
$R^6$ is hydrogen, alkyl, aryl, or carboxyalkyl;
X is —S(O)$_2$—, —S(O)$_2$—NH—, —C(O)—, —C(O) $NR^6$ or C(O)—O— or a dimeric form, or a pharmaceutically acceptable ester, or a pharmaceutically acceptable salt thereof, preferably a pharmaceutically acceptable ester, or a pharmaceutically acceptable salt thereof, and most preferably a pharmaceutically acceptable salt thereof.

In a preferred embodiment, the invention refers to compounds wherein $R^1$ is hydrogen.

In a further preferred embodiment of the present invention $R^2$ is alkyl, halogenalkyl, alkylamino, alkoxy, cycloalkyl, cycloalkylamino, aryl, arylalkyl, aryloxy, arylalkylamino, arylalkoxy, heteroaryl, amino, or (mono- and dialkyl)amino; more preferably alkyl, halogenalkyl, alkylamino, alkoxy, cycloalkyl, cycloalkylamino, aryl, arylalkyl, or heteroaryl and even more preferably is aryl or heteroaryl and most preferably aryl. The term aryl in the definition for $R^2$ especially means naphthyl or phenyl, wherein phenyl is optionally substituted by one or more fluor or by one phenyl group, e.g. $R^2$ is naphthyl, 2,3,4,5,6-pentafluorophenyl or biphenyl.

According to the present invention $R^3$ is preferably hydrogen or alkyl, most preferably hydrogen.

In the above compounds $R^4$ is preferably hydrogen, arylalkyl, alkyl, arylsulfonyl, heteroarylsulfonyl, cycloalkylalkyl, or carboxyalkyl, more preferably hydrogen, alkyl, arylalkyl, cycloalkyl, arylsulfonyl, or carboxyalkyl, most preferably hydrogen, alkyl, cycloalkyl, carboxyalkyl or arylalkyl, even more preferably hydrogen, alkyl or arylalkyl, e.g. hydrogen, 2,4,5-trifluorobenzyl, 2,4-difluorobenzyl, benzyl, methyl, ethyl, isopropyl, isobutyl, benzyl or HO$_2$C—CH$_2$—, or cycloalkylpropylmethyl.

In a preferred embodiment of the present invention R$^5$ is hydrogen, alkylcarbonyl, alkoxycarbonyl, alkylsulfonyl, aryl, arylalkyl, arylcarbonyl, (mono- and dialkylamino) alkylcarbonyl, (mono- and dialkyl)aminosulfonyl, arylalkoxycarbonyl, arylaminocarbonyl, arylsulfonyl, heteroarylcarbonyl, heteroarylalkylcarbonyl, heteroarylsulfonyl, arylaminocarbonyl, heteroaryl, or heterocyclyl, more preferably aryl, arylalkyl, arylcarbonyl, arylalkoxy, arylaminocarbonyl, arylsulfonyl, heteroarylcarbonyl, heteroarylalkylcarbonyl, heteroarylsulfonyl, arylaminocarbonyl, heteroaryl, or heterocyclyl, more preferably arylsulfonyl, arylalkyl, heteroarylalkylcarbonyl, heteroarylsulfonyl and most preferably 4-methyl-benzenesulfonyl, benzyl, 4-methoxybenzenesulfonyl, (1H-indol-3-yl)acetyl, thiophene-2-yl, or 3,5-dimethyl-isoxyzolyl-4-sulfonyl.

In the above described compounds X is preferably —SO$_2$—, —C(O)—, and most preferably —SO$_2$—.

In the most preferred embodiment of the present invention, the compounds maybe described by the formula (II)

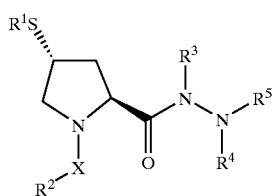

(II)

wherein R$^1$, R$^2$, R$^3$, R$^4$, R$^5$ and X are as defined above and pharmaceutically acceptable esters and/or salts thereof.

In a further preferred embodiment of the present invention R$^1$ is hydrogen, R$^2$ is naphthyl or phenyl, wherein phenyl is optionally substituted by one or more fluor or by one phenyl group, R$^3$ is hydrogen or alkyl, R$^4$ is hydrogen, alkyl or arylalkyl, R$^5$ is arylsulfonyl, arylalkyl, heteroarylalkylcarbonyl, heteroarylsulfonyl; and X is —SO$_2$—.

Preferred embodiments of the present invention are the compounds exemplified in the examples. Especially the present invention comprises compounds according to formula (I) or (II)

(2S,4R)-4-Mercapto-1-(naphthalene-2-sulfonyl)-pyrrolidine-2-carboxylic acid N'-isobutyl-N'-(4-methyl-benzenesulfonyl)-hydrazide;

(2S,4R)-4-Mercapto-1-(naphthalene-2-sulfonyl)-pyrrolidine-2-carboxylic acid N'-(4-methyl-benzenesulfonyl)-hydrazide;

(2S,4R)/4-Mercapto-1-(naphthalene-2-sulfonyl)-pyrrolidine-2-carboxylic acid N'-benzyl-hydrazide;

(2S,4R)-4-Mercapto-1-(naphthalene-2-sulfonyl)-pyrrolidine-2-carboxylic acid N'-benzyl-N'-(4- methyl-phenylsulfonyl)-hydrazide;

(2S,4R)-4-Mercapto-1-(naphthalene-2-sulfonyl)-pyrrolidine-2-carboxylic acid N'-methyl-N'-(4-methyl-benzenesulfonyl)-hydrazide;

(2S,4R)-4-Mercapto-1-(naphthalene-2-sulfonyl)-pyrrolidine-2-carboxylic acid N'-benzenesulfonyl-hydrazide;

(2S,4R)-4-Mercapto-1-(naphthalene-2-sulfonyl)-pyrrolidine-2-carboxylic acid N'-(4-methoxy-benzenesulfonyl)-hydrazide;

(2S,4R)-4-Mercapto-1-(naphthalene-2-sulfonyl)-pyrrolidine-2-carboxylic acid N'-[(1H-indol-3-yl)-acetyl]-hydrazide;

(2S,4R)-4-Mercapto-1-(naphthalene-2-sulfonyl)-pyrrolidine-2-carboxylic acid N'-thiophene-2-sulfonyl-hydrazide;

(2S,4R)-4-Mercapto-1-(naphthalene-2-sulfonyl)-pyrrolidine-2-carboxylic acid N'-(3,5-dimethyl isoxazole-4-sulfonyl)-hydrazide;

(2S,4R)-4-Mercapto-1-(naphthalene-2-sulfonyl)-pyrrolidine-2-carboxylic acid N'-cyclopropylmethyl-N'-(4-methyl-benzenesulfonyl)-hydrazide;

(2S,4R)-4-Mercapto-1-(naphthalene-2-sulfonyl)-pyrrolidine-2-carboxylic acid N'-(4-methyl-benzenesulfonyl)-N'-(2,4,5-trifluoro-benzyl)-hydrazide;

(2S,4R)-4-Mercapto-1-(naphthalene-2-sulfonyl)-pyrrolidine-2-carboxylic acid N'-(2,5-difluoro-benzyl)-N'-(4-methyl-benzenesulfonyl)-hydrazide (2S,4R)-4-Mercapto-1-(naphthalene-2-sulfonyl)-pyrrolidine-2-carboxylic acid N'-isopropyl-N'-(4-methyl-benzensulfonyl)-hydrazide;

(2S,4R)-[N'-[4-Mercapto-1-(naphthalene-2-sulfonyl)-pyrrolidine-2-carbonyl]-N-(4-methyl-benzenesulfonyl)-hydrazino]-acetic acid;

(2S,4R)-1-(Biphenyl-4-sulfonyl)-4-mercapto-pyrrolidine-2-carboxylic acid N'-methyl-N'-(4-methyl-benzenesulfonyl)-hydrazide;

(2S,4R)-4-Mercapto-1-(2,3,4,5,6-pentafluoro-benzenesulfonyl)-pyrrolidine-2-carboxylic acid N'-(4-methyl-benzenesulfonyl)-hydrazide;

(2S,4R)-4-Mercapto-1-(naphthalene-2-sulfonyl)-pyrrolidine-2-carboxylic acid N'-benzyl-N'-(4-methoxy-benzenesulfonyl)-hydrazide;

(2S,4R)-4-Mercapto-1-(naphthalene-2-sulfonyl)-pyrrolidine-2-carboxylic acid N-methyl-N'-(4-methyl-benzenesulfonyl)-hydrazide; and (2S,4R)-4-Mercapto-1-(naphthalene-2-sulfonyl)-pyrrolidine-2-carboxylic acid N-methyl-N'-benzyl-N'-(4-methyl-benzenesulfonyl)-hydrazide.

These compounds show IC$_{50}$ values in the radioimmunoassay (E on ECE-inhibition, see below) of about 50 nM to 1 μM.

The invention also refers to pharmaceutical compositions containing a compound as defined above and a pharmaceutically acceptable excipient.

A further embodiment of the present invention refers to the use of compounds as defined above as active ingredients in the manufacture of medicaments comprising a compound as defined above for the prophylaxis and treatment of disorders which are caused by endothelin-converting enzyme (ECE) activity especially myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection.

Further the invention refers to the use of compounds as described above for the treatment or prophylaxis of diseases which are associated with myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection.

In addition the invention comprises compounds as described above for use as therapeutic active substances, in particular in context with diseases which are associated with zinc hydrolase activity such as myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection.

The invention also comprises a method for the therapeutic and/or prophylactic treatment of myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection, which method comprises administering a compound as defined above to a human being or animal.

The invention also relates to the use of compounds as defined above for the inhibition of zinc hydrolase activity.

The invention relates also to a process for the preparation of a compound as defined above comprising reaction of a compound of formula III

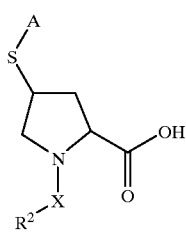

(III)

wherein
$R^1$, $R^2$, and X are as defined above and A is a HS-protecting group with $HNR^3NR^4R^5$ for introduction of a hydrazide: or
$HNR^3NR^4R^5$ with $R^5$ as protecting group followed by conversion or introduction of $R^3$ and $R^4$; optionally followed by conversion of a $R^5$ and/or $R^2$—X group into a different $R^5$ and/or $R^2$—X group and/or deprotection and or thiol liberation and wherein $R^3$, $R^4$ and $R^5$ are as defined above.

The invention also refers to the above compounds whenever manufactured by a process as described.

The compounds of formula (I) can be prepared by methods known in the art or as described below.

Unless otherwise indicated, the substituents $R^1$, $R^2$, $R^3$, $R^4$, $R^5$, $R^6$, and X are as described above. In the schemes below, all starting materials are known or can be prepared by known methods.

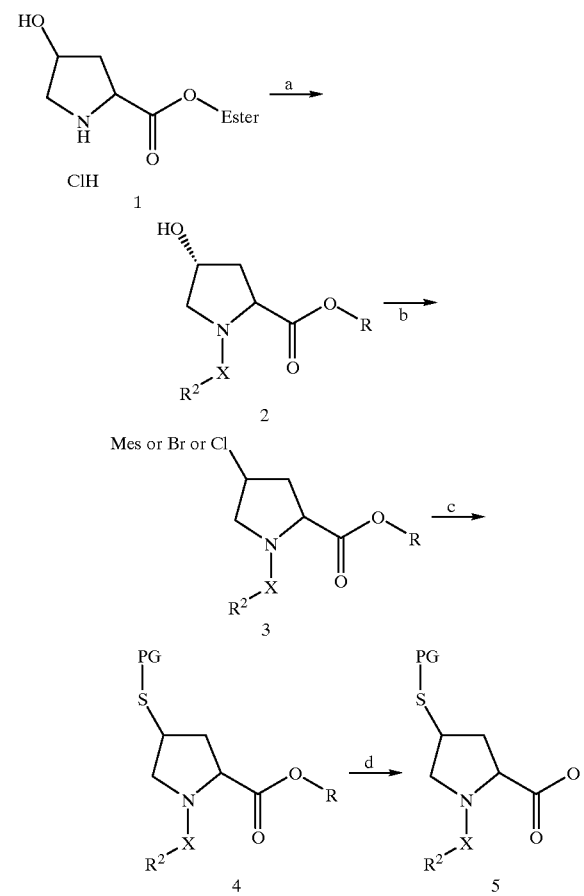

PG = protecting group such as trityl or PMB

Step a) of scheme 1 describes the persilylation of hydroxy- and amino groups, e.g. by reaction of compound 1 with hexamethyldisilazan/140° C. followed by reaction with $R^2SO_2Cl$ in THF or conversion to all other $R^2X$ described later or di-t-butyldicarbonate/NaHCO$_3$ in dioxane/H$_2$O (BOC protection). For inversion of the configuration (via mesylate) the resulting alcohol 2 is treated with MeSO$_3$H/Ph$_3$P/DIAD in toluene (room temperature to 80° C.) or (via bromide) with LiBr/DEAD/Ph$_3$P in THF (4° C. to room temperature) or (via chloride) with Ph$_3$P/CCl$_4$ in CH$_2$Cl$_2$ (3° C. to room temperature). In case of retention of the configuration (via mesylate) alcohol 2 can be transformed to a compound of formula 3 by reaction with MeSO$_2$Cl/pyridine/DMAP (0° C. to room temperature).

For the introduction of a protected thiol moiety, compounds of formula 3 are treated with e.g. triphenylmethanethiol or 4-methoxybenzylmercaptane and K-Ot-Bu in DMF (for Br: 0° C. to room temperature; for Cl: 0° C.; for Mesylate: room temperature to 100° C.). Hydrolysis of ester 4 with aqueous LiOH in THF (0° C. to RT) gives acid 5.

The synthesis of final compounds are shown in scheme 2:

The synthesis starts with a preactivation af acid 1a (N-hydroxy-2-pyridone, N,N-dicyclohexylcarbodiimide, 4-Ethylmorpholine in CH$_2$Cl$_2$ at RT) followed by reaction with an alkyl-hydrazine (NHR$^3$NHR$^4$) (step a) or for carboxylic acid hydrazide 2 ($R^3$, $R^4$, $R^5$=H), ester 1b is directly treated with hydrazine (NH$_2$NH$_2$.H$_2$O) in EtOH (at RT). Conversion to the free thiol 3 is done in the following way: in case PG (protecting group) is Tr by reaction with e.g. TFA/Et$_3$SiH at 0° C. to room temperature or, in case PG is PMB, by reaction with e.g. TFA/Et$_3$SiH, at 0 to 80° C. (step b).

In the case of carboxylic acid hydrazide 2 ($R^3$, $R^4$, $R^5$=H), $R^4$ is introduced by reductive amination: Imine formation with an aldehyde in EtOH followed by reduction with $NaBH_3CN$ in THF gives compound 4 (step c). For the introduction of a new $R^5$ in case $R^4$ is an alkyl ($R^5$=H), reaction with $ClCOR^5$, $ClCO_2R^5$, $ClSO_2R^5$ or $ClSO_2NR^5$, $iPr_2NEt$ or Huenig's base $CH_2Cl_2$ in the precence of a catalytic amount of DMAP or DMAP-poly or $R^5NCO$ in THF at room temperature gives compound 4 which is deprotected to the final thiol 5 as described above (step c and b).

Selective BOC deprotection of compound 2 or 4 (TFA, $CH_2Cl_2$ at 0° C.), followed by reaction with $ClCO_2R_2$, NEM or $iPr_2NEt$, $CH_2Cl_2$ or $R^2NCO$ in THF at 0° C. to room temperature (or conversion to all other $R^2X$ described for $R^5$— introduction above) gives compound 7 (step e). Thiol deprotection as described above gives the final thiol 8 (step b).

Scheme 3 shows a different way for the synthesis of hydrazides.

Preactivation af acid 1 (N-hydroxy-2-pyridone, N,N-dicyclohexylcarbodiimide, 4-Ethylmorpholine in $CH_2Cl_2$ at RT) followed by reaction with an alkyl-hydrazinecarboxylic acid benzyl ester ($NHR^3NHR^4$) (step a) gives hydrazide 2 which is converted with HBr in AcOH at 0° C. to 3 (step b). A direct conversion from 1 to 3 with preactivation and reaction with $NHR^3NR^4 R^5$ is possible too (step c). Introduction of a new $R^3$ is done with an $R^3$-halogenide/ NaH in DMF (at 0° C. to RT; ->4, step e). Deprotection to the thiol 5 is done in the following way: in case PG is Tr by reaction with e.g. $TFA/Et_3SiH$ at 0° C. to room temperature or, in case PG is PMB, by reaction with e.g. $TFA/Et_3SiH$, at 0 to 80° C. (step d).

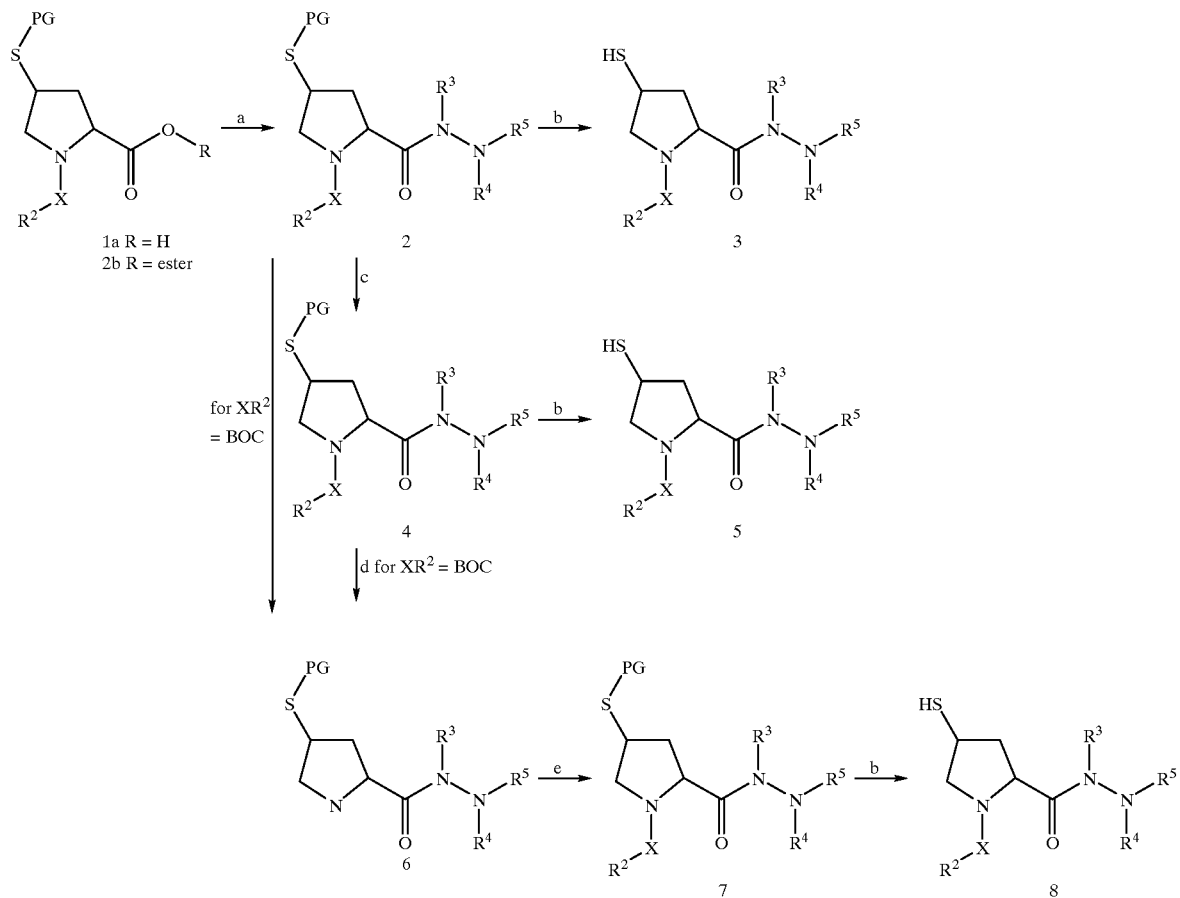

Scheme 2

Scheme 3

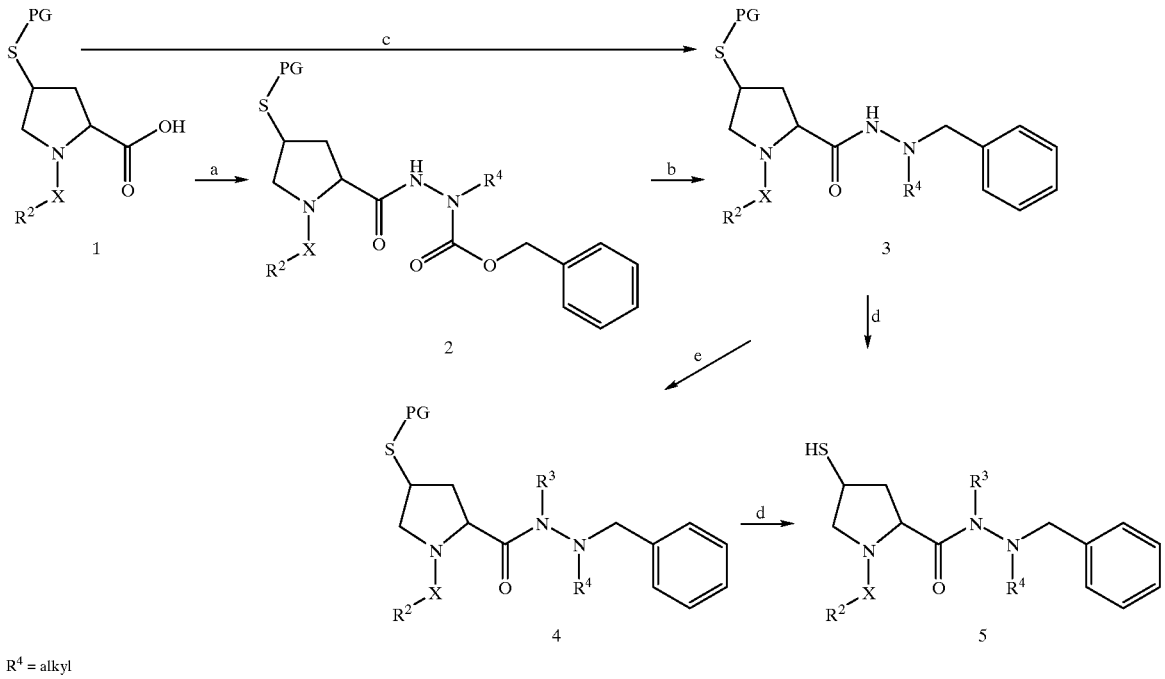

$R^4$ = alkyl

Scheme 4 shows an other way for the synthesis of hydrazides.

Preactivation af acid 1 (N-hydroxy-2-pyridone, N,N-dicyclohexylcarbodiimide, 4-Ethylmorpholine in $CH_2Cl_2$ at RT) followed by reaction with a tert-butyl 2-alkyl-hydrazinecarboxylate ($NHR^3NHBOC$) (step a) gives hydrazide 2 which by treatment with triethylsilane in TFA at 0 to 80° C. gives thiol 3 (step b). Alkylation with alkylhalogenide ($R^5$-halogenide) and DMF with NaH as base (at 0° C. to RT) results in compound 4 which gives after $Et_3SiH$/TFA deprotection (as described in scheme 1) thiol 5 (step c, d).

Selective BOC-deprotection (TFA in $CH_2Cl_2$->6) followed by reaction with $ClCO_2R^4$, $ClSO_2R^4$, $iPr_2NEt$ or NEM in $CH_2Cl_2$ in the precence of a catalytic amount of DMAP or DMAP-poly at room temperature gives compounds 7 ($R^4$=$R^5$) and 8 which are separated and deprotected ($Et_3SiH$/TFA as described in scheme 1) to thiol 5 (step e, f and d). The not fully substituted hydrazide 8 can be further alkylated ($R^5$-halogenide and DMF/NaH, 0° C. to RT) and deprotected ($Et_3SiH$/TFA as described in scheme 1) to the thiol 5 (step g and d).

Scheme 4

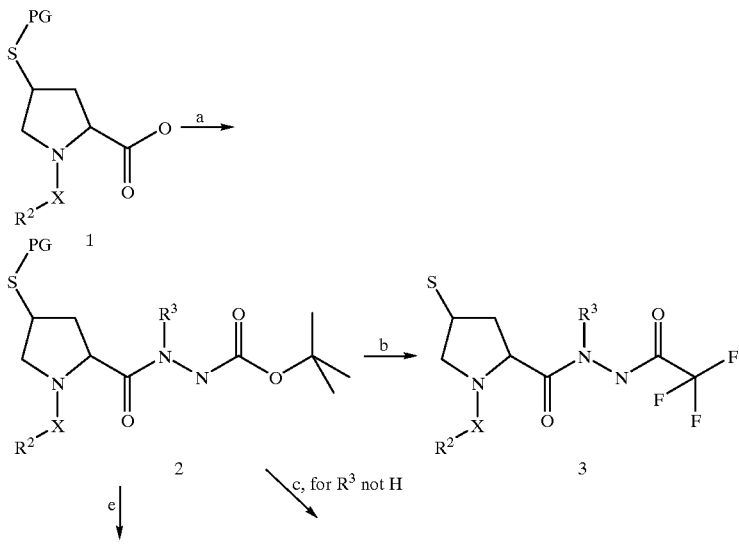

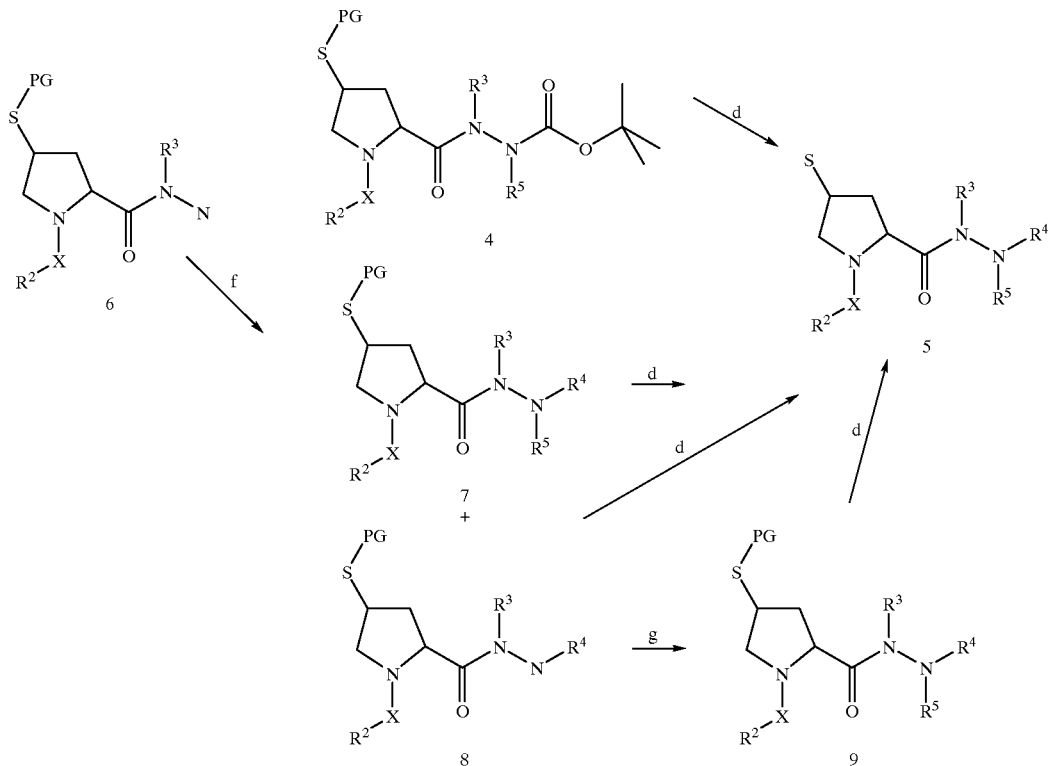

Scheme 5 shows further transformation of hydrazide 1. Acylation with γ-Bromo-alkanoyl chloride in the presence of iPr$_2$EtN in THF (0° C. to RT) gives compound 2 which is cyclised (NaH in DMF at RT). Separation of the two isomers and deprotection of the thiol (Et$_3$SiH/TFA as described in scheme 1) gives hydrazides 3 and 4.

Scheme 5

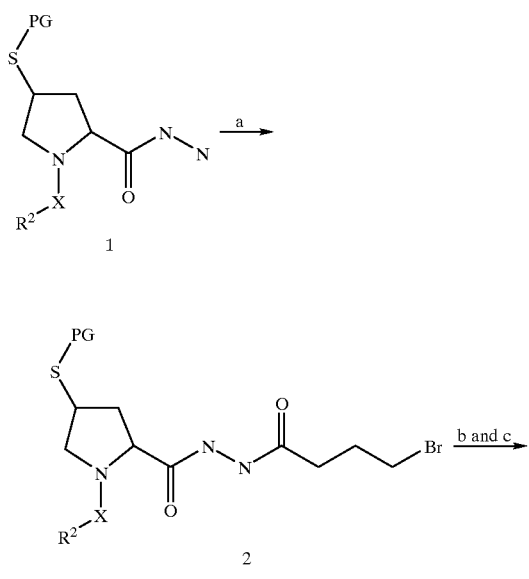

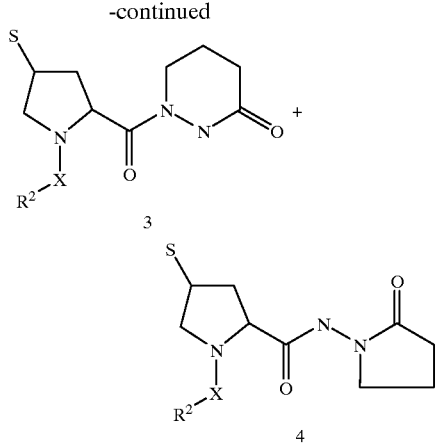

For the preparation of compounds of formula 5 the reaction pathway of scheme 6 can be followed: the synthesis of the starting material 1 from hydroxyproline is described in scheme 1. TFA/triisopropyl deprotection at reflux for 30 minutes gives thiol 2 that is attached to the resin. The final R$^2$X is introduced either at the beginning or after manipulations at NR$^3$NR$^4$R$^5$ (scheme 9). In the second case, R$^2$X (=BOC) of starting acid 1 is transformed by methods known in the art and described for example in "The Practice of Peptide Synthesis", M. Bodanszky and A. Bodanszky, Springer Verlag, Berlin, 1984 to a nonacid labile protecting group (e.g. R$^2$X=FMOC, step a: first selective BOC-deprotection with 40% TFA in CH$_2$Cl$_2$ at RT followed by reaction with Fmoc-OSu in dioxane/water and NaHCO$_3$ as base).

Scheme 6
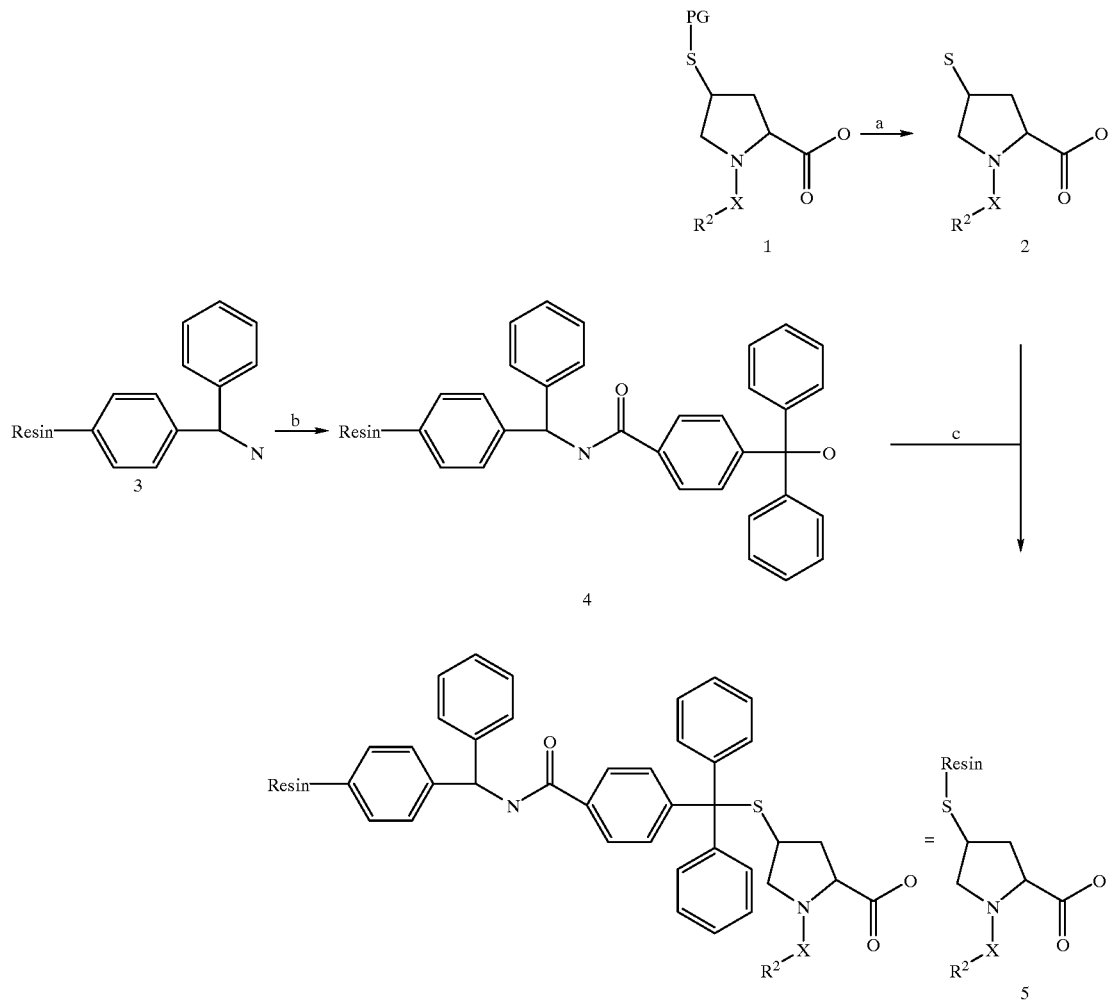
The resin is prepared as follows (step b): The linker 4-(α,α-diphenylhydroxymethyl)benzoic acid is activated using TPTU, DIEA in DMF and added to benzhydrylamine resin 3. The resin is then treated with thiol 2 in $CH_2Cl_2$/TFA to give the resin loaded starting material 5.
Scheme 7
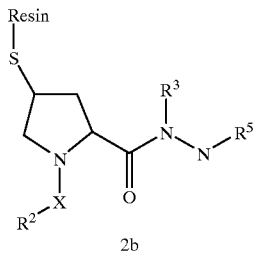

-continued

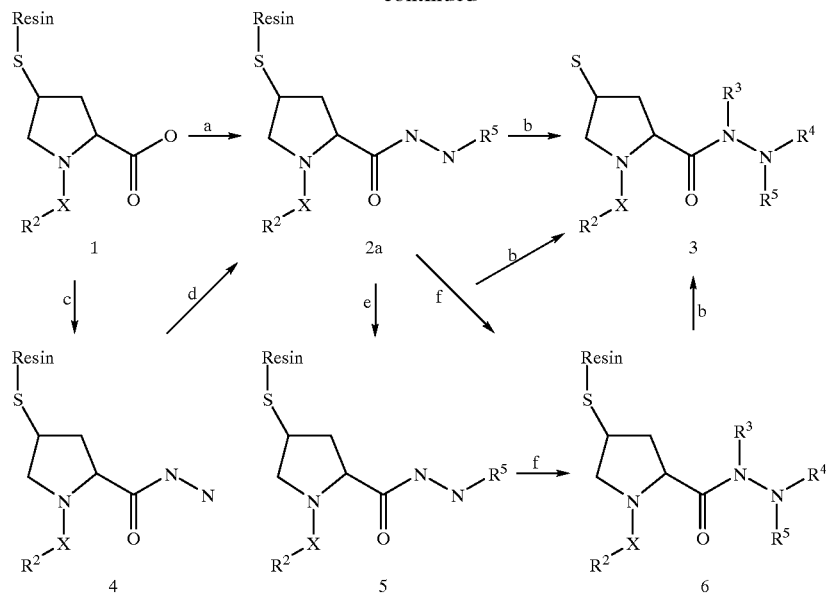

The synthesis of final compounds on resin 1 is shown in scheme 7: The synthesis starts with a preactivation af acid 1 (TPTU, Huenig's base in DMF at RT) followed by reaction with an alkyl-hydrazine ($NH_2NHR^4$) (step a) to give intermediates 2a, 2b or 4 ($R^3$, $R^4$, $R^5$=H, step c). Detachment of the resin to the free thiol 3 is done with $TFA/iPr_3SiH$ in $CH_2Cl_2$ at RT (step b). In the case of carboxylic acid hydrazide 4, the introduction of a new $R^5$ is done by reaction with $ClCOR^5$, $ClCO_2R^5$, $ClSO_2R^5$ or $ClSO_2NR^5$, in DMF to give compound 2 which is optionally alkylated (alkyl halgenide/DBU in DMF) to the disubstituted hydrazide 6 (step d and f). Detachment of the resin as described above gives the final thiol 3. In the case of reaction of hydrazide 4 with $ClSO_2R^5$, double sulfonylation to compound 2a and 2b takes place (step d), these compounds can be separated after detachment from the resin as the corresponding thiol 3.

If $R^2X$ is FMOC: Deprotection of compound 2 (20% piperidine/DMF then reaction with $ClCO_2R^2$, pyridine, DMF or $R^2NCO$ in DMF at RT or conversion to all other $R^2X$ described for $R^4$— introduction above) gives compound 5 (step e). Alkylation (alkyl halgenide/DBU in DMF) and resin deprotection as described above gives the final thiol 3 (step f and b).

The ability of the compounds of formula (I) to inhibit metalloprotease activity, particularly zinc hydrolase activity, may be demonstrated by a variety of in vitro and in vivo assays known to those of ordinary skill in the art.

A) Cell Culture

A stable human umbilical vein endothelial cell line (ECV304) was cultured in "cell factories" as described until confluency (Schweizer et al. 1997, Biochem. J. 328: 871–878). At confluency cells were detached with a trypsin/EDTA solution and collected by low speed centrifugation. The cell pellet was washed once with phosphate buffered saline pH 7.0 and stored at −80° C. until use.

B) Solubilization of ECE from ECV304 cells

All procedures were performed at 0–4° C. if not stated otherwise. The cell pellet of $1 \times 10^9$ cells was suspended in 50 ml of buffer A (20 mM Tris/HCl, pH 7.5 containing 5 mM $MgCl_2$, 100 μM PMSF, 20 μM E64, 20 μM leupeptin) and sonicated. The resulting cell homogenate was centrifuged at 100,000 $g_{av}$ for 60 minutes. The supernatant was discarded and the resulting membrane pellet was homogenized in 50 ml buffer A and centrifugated as described. The washing of the membrane fraction in buffer A was repeated twice. The final membrane preparation was homogenized in 50 ml of buffer B (buffer A+0.5% Tween 20 (v/v), 0.5% CHAPS (w/v), 0.5% Digitonin (w/v)) and stirred at 4° C. for 2 hours. Thereafter the remaining membrane fragments were sedimented as described. The resulting clear supernatant containing the solubilized ECE was stored in 1.0 ml aliquots at −120° C. until use.

C) ECE Assay

The assay measured the production of ET-1 from human big ET-1. To measure high numbers of samples an assay performed in 96 well plates was invented. The enzyme reaction and the radioimmunological detection of the produced ET-1 was performed in the same well, using a specifically developed and optimized coating technique.

D) Coating of Plates

Fluoronunc Maxisorp White (code 437796) 96 well plates were irradiated with 1 joule for 30 minutes in a UV Stratalinker 2400 (Stratagene). The 96 well plates were then fill with 300 μl protein A solution (2 μg/ml in 0.1 M $Na_2CO_3$ pH 9.5) per well and incubated for 48 hours at 4° C. Coated plates can be stored for up to 3 weeks at 4° C. until use.

Before use the protein A solution is discarded and the plates are blocked for 2 hours at 4° C. with 0.5% BSA in 0.1M $Na_2CO_3$, pH 9.5.

Plates were washed with bidestilled water and were ready to perform the ECE assay.

E) Screening Assay

Test compounds are solved and diluted in DMSO. 10 μl of DMSO was placed in the wells, followed by 125 μl of assay buffer (50 mM Tris/HCl, pH 7.0, 1 μM Thiorphan, 0,1% $NaN_3$, 0.1% BSA) containing 200 ng big ET-1. The enzyme reaction was started by the addition of 50 μl of solubilized ECE (diluted in assay buffer 1:30 to 1:60 fold (v/v)). The enzyme reaction was carried out for 30 minutes at 37° C. The enzyme reaction was stopped by addition of 10 μl 150 mM ETDA, pH 7.0.

Radioimmunoassay

The ET-1 RIA was performed principally as described earlier (Löffler, B.-M. and Maire, J.-P. 1994, Endothelium 1:

273–286). To plates containing the EDTA stopped enzyme reaction mixture 25 μl of assay buffer containing 20000 cpm (3-($^{125}$I)Tyr)-endothelin-1 and 25 μl of the ET specific antiserum AS-3 (dilution in assay buffer 1:1000) was added. Plates were incubated under mixing at 4° C. over night. Thereafter, the liquid phase was sucked with a plate washer and plates were washed once with bidestilled water. To the washed plates 200 μl scintillation cocktail (Microscint 40 LSC-Cocktail, Packard, code 6013641) was added and plates were counted for 2 minutes per well in a Topcount.

Standard curves were prepared in plates with synthetic ET-1 with final concentrations of 0 to 3000 pg ET-1 per well. In all plates controls for maximal ECE activity (in the presence of 10 μl DMSO) and for background production of ET-1 immunoreactivity (in the presence of 10 mM EDTA or 100 μM phosphoramidon) were performed. Assays were run in triplicate.

F) Kinetic Assay

The described assay format could be used to determine the kinetic characteristics of the used ECE preparation as well as different ECE inhibitors (i.e. Km, Ki) by variation of the substrate concentration used in the assay.

G) Cell based ECE Assay

Human ECE-1c was stable expressed in MDCK cells as described (Schweizer et al. 1997, Biochem. J. 328: 871–878). Cells were cultured in 24 well plates to confluency in Dulbecco's modified Eagles's medium (DMEM) supplemented with 10% (v/v) fetal bovine serum (FBS), 0.8 mg/ml geneticin, 100 i.u./ml penicillin and 100 μg/ml streptomycin in a humidified air/$CO_2$ (19:1) atmosphere. Before ECE assay the medium was replaced by 0.5 ml DMEM-HBSS 1:1, 10 mM HEPES pH 7.0 supplemented with 0.1% (w/v) BSA. The inhibitors were added in DMSO at a final concentration of 1%. The enzyme reaction was started by the addition of 0.42 μM human big ET-1 and performed for 1.5 hours at 37° C. in an incubator. At the end of incubation, the incubation medium was quickly removed and aliquots were analysed by radioimmunoassay for produced ET-1 as described above.

The ECE screening assay was validated by the measurement of the characteristic inhibitor constants of phosphoramidon ($IC_{50}$ 0.8±0.2 μM) and CGS 314447 ($IC_{50}$ 20±4 nM) [De Lombaert, Stephane; Stamford, Lisa B.; Blanchard, Louis; Tan, Jenny; Hoyer, Denton; Diefenbacher, Clive G.; Wei, Dongchu; Wallace, Eli M.; Moskal, Michael A.; et al. Potent non-peptidic dual inhibitors of endothelin-converting enzyme and neutral endopeptidase 24.11. Bioorg. Med. Chem. Lett. (1997), 7(8), 1059–1064]. The two inhibitors were measured with $IC_{50}$ values not significantly different from those described in the literature but measured with different assay protocols. In the cell based assay phosphoramidon showed an $IC_{50}$ of 4 μM. This assay gave additional information about the inhibitory potency of inhibitors under much more physiologic conditions, as e.g. the ECE was embedded in a normal plasma membrane environment. It is important to state, that the screening assay was performed in the presence of 1 μM Thiorphan to block any potential big ET-1 degradation due to the action of NEP24.11. No NEP activity was present in MDCK-ECE-1c transfected cells in preliminary experiments when ET-1 production was measured in presence or absence of thiorphan. In subsequent experiments no thiorphan was added in the incubation medium.

According to the above methods, the compounds of the present invention show $IC_{50}$ values in the radioimmunoassay (E on ECE-inhibition) of about 50 nM to about 1000 μM. The preferred compounds show values of 50 nM to 1 μM.

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, dragees, hard or soft gelatin capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatin capsules the compounds of the present invention may be admixed with pharmaceutically inert, inorganic or organic excipients. Examples of suitable excipients for tablets, dragees or hard gelatin capsules include lactose, maize starch or derivatives thereof, talc or stearic acid or salts thereof.

Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, alcohols, polyols, glycerin, and vegetable oils.

For suppositories, and local or percutaneous application, excipients which may be used include for example natural or hardened oils, waxes, fats and semi-solid or liquid polyols.

The pharmaceutical compositions may also contain preserving agents antioxidants, solubilising agents, stabilizing agents, wetting agents, emulsifiers, sweeteners, colorants, odorants, salts for the variation of osmotic pressure, buffers, coating agents or antioxidants. They may also contain other therapeutically valuable agents.

The dosages in which the compounds of formula I are administered in effective amounts depend on the nature of the specific active ingredient, the age and the requirements of the patient and the mode of application. In general, dosages of 0.1–100 mg/kg body weight per day come into consideration, although the upper limit quoted can be exceeded when this is shown to be indicated.

The following specific examples are provided as a guide to assist in the practice of the invention, and are not intended as a limitation on the scope of the invention.

EXAMPLES

General Remarks

All reactions were done under argon.

Abbreviations: EtOH Ethanol, THF Tetrahydrofuran, $Et_2O$ Diethylether, MeOH Methanol, $CH_2Cl_2$, EDCI N-(3-Dimethylaminopropyl)-N'-ethylcarbodiimide hydrochloride, HOBT 1-Hydroxybenzotriazole, DBU 1,8-Diazabicyclo[5.4.0]undec-7-ene(1,5-5), LAH Lithium aluminium hydride, LDA lithium diisopropylamide, DEAD Diethyl azodicarboxylate, DIAD Diisopropyl azodicarboxylate, DMAP 4-Dimethylaminopyridine, DMAP-poly 4-(N-Benzyl-N-methylamino)pyridine, polymer-supported (polystyrol based 2%DVB, ca 1,6 mmol "DMAP"/g resin), NEM N-ethylmorpholine, NMM N-methylmorpholine, TBAF tetrabutylammonium fluoride, DIEA diethylamine, DMF dimethylformamide, TFA trifluoroacetic acid, TPTU 2-(2-pyridon-1-yl)-1,1,3,3-tetramethyl uronium tetrafluorobrate, iPr₂NEt Huenigs base or N-ethyldiisopropylamine, FMOC-OSu 9-Fluorenylmethyloxycarbonyl-N-hydroxysuccinimide ester.

Example 1

Starting Materials (Esters—Scheme 1)

40 g (220 mmol) of L-hydroxyproline methylester-hydrochloride (twice suspended in toluene and evaporated under reduced pressure to remove water) was suspended in 600 ml hexamethyldisilazane and refluxed for 2 h. The solution was evaporated under reduced pressure and dissolved in 100 ml THF. 49.9 g (220 mmol) of 2-naphthalene-sulfonyl chloride in 200 ml of THF were added slowly and stirred for 16 h at RT. 150 ml H₂O were added and after 1 h the solvents were evaporated. The residue was partitioned between water/ethyl acetate (3×), the organic phases were washed with 10% NaCl and dried over Na₂SO₄ to give 60.4 g (82%) of (2S,4R)-4-Hydroxy-1-(naphthalene-2-sulfonyl)-pyrrolidine-2-carboxylic acid methyl ester, MS: 335 (M⁺).

Scheme 1

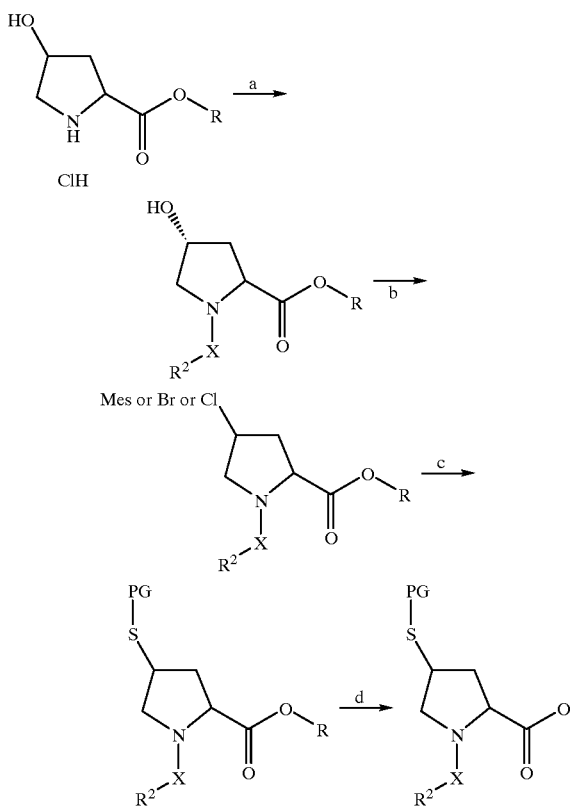

In analogy L-hydroxyproline benzylester-hydrochloride and 1-naphthalenesulfonyl chloride gave (2S,4R)-4-Hydroxy-1-(naphthalene-2-sulfonyl)-pyrrolidine-2-carboxylic acid benzyl ester, MS: 411 (MH⁺); L-hydroxyproline benzylester-hydrochloride and methanesulfonyl chloride gave (2S,4R)-4-Hydroxy-1-methanesulfonyl-pyrrolidine-2-carboxylic acid benzyl ester, mp 132–133° C., MS: 300 (MH⁺); L-hydroxyproline methylester-hydrochloride and methanesulfonyl chloride gave after extraction with CH₂Cl₂ (2S,4R)-4-Hydroxy-1-methanesulfonyl-pyrrolidine-2-carboxylic acid methyl ester, mp 115.5–117° C., MS: 164 (M−COOMe⁻).

Via Mesylate: A biphasic solution of 13.9 ml (215 mmol) methanesulfonic acid, 29.8 ml (215 mmol) triethylamine and 58.7 g (224 mmol) triphenylphosphine in 150 ml toluene was added to a suspension of 60 g (179 mmol) (2S,4R)-4-Hydroxy-1-(naphthalene-2-sulfonyl)-pyrrolidine-2-carboxylic acid methyl ester in 300 ml toluene which was stirred mechanically. After adding 44.9 ml (233 mmol) of diisopropyl azodicaboxylate (exothermic!) the solution was heated for 2.5 h at 80° C. 300 ml water was added at RT and extracted with ethylacetate (3×300 ml). The organic phase was washed with aqueous 10% KHSO₄ (2×100 ml), 10% NaCl (2×150 ml), dried over Na₂SO₄ and evaporated to give 180 g of crude product. Flash chromatography (ethyl acetate/hexane 1:1) gave 63.7 g (86%) of (4S, 2S)-4-Methanesulfonyloxy-1-(naphthalene-2-sulfonyl)-pyrrolidine-2-carboxylic acid methylester.

64.2 g (167 mmol) of triphenylmethanthiol was slowly added at RT to a solution of 17.9 g (160 mmol) of potassium tert-butylate in 300 ml DMF and stirred mechanically for 30 min. Then 63 g (152 mmol) of (4S, 2S)-4-Methanesulfonyloxy-1-(naphthalene-2-sulfonyl)-pyrrolidine-2-carboxylic acid methylester in 300 ml DMF were added at 20° C. by cooling at the end with an ice bath. The reaction was heated for 1.3 h at 100° C., cooled, evaporated to 400 ml and extracted with 250 ml aqueous saturated NH₄Cl/ethyl acetate (3×300). The organic phases were washed with aq. 10% NaCl, dried (Na₂SO₄) and evaporated. Flash chromatography (CH₂Cl₂/MeOH 99:1) gave 58.6 g (65%, (2S,4R)/(2R,4R)-isomer ca 4:1, ¹H-NMR) and 9.2 g (10%, (2S,4R)/(2R,4R)-isomer ca 1:1, ¹H-NMR) of (2S,4R)-1-(Naphthalene-2-sulfonyl)-4-tritylsulfanyl-pyrrolidine-2-carboxylic acid methyl ester, MS: 594 (MH⁺).

In analogy: (2S,4R)-4-Hydroxy-1-methanesulfonyl-pyrrolidine-2-carboxylic acid methyl ester gave after 3.75 h at 80° C. (4S, 2S)-4-Methanesulfonyloxy-1-(methylsulfonyl)-pyrrolidine-2-carboxylic acid methylester which was heated for 45 min at 100° C. with triphenyl-methanthiolate to give (2S,4R)-1-Methanesulfonyl-4-tritylsulfanyl-pyrrolidine-2-carboxylic acid methyl ester ((2S,4R)/(2R,4R)-isomer ca 9:1, ¹H-NMR), MS: 482 (MH⁺); (2S,4R)-4-Hydroxy-1-methanesulfonyl-pyrrolidine-2-carboxylic acid benzyl ester gave after 5 h at 80° C. (2S,4S)-1-Methanesulfonyl-4-methanesulfonyloxy-pyrrolidine-2-carboxylic acid benzyl ester which was heated for 30 min with 4-methoxybenzylthiol/potassium tert-butylate to give (2S,4S)-1-Methanesulfonyl-4-methanesulfonyloxy-pyrrolidine-2-carboxylic acid benzyl ester, mp 91–92° C., MS: 453 (M+NH4⁺).

Via bromide: To a solution of 76.5 g (291.6 mmol, 6 eq) triphenylphosphine in 650 ml THF were added 44.6 ml (286.8 mmol, 5.9 eq) DEAD in 70 ml THF at a temperature between 1.5–4.5° C. over a period of 0.5 h. The solution was stirred for 0.5 h before 42.2 g (486.1 mmol, 10 eq) LiBr were added, and the reaction mixture was recooled to 4° C. for the addition of 20 g (48.6 mmol) (2S,4R)-4-Hydroxy-1-(naphthalene-2-sulfonyl)-pyrrolidine-2-carboxylic acid benzyl ester in 75 ml THF. After stirring at RT for 3 h, water was added and the suspension concentrated and redissolved in 700 ml ethyl acetate and water. The layers were separated, the inorganic one was extracted with 100 ml of ethyl acetate (3×), and the combined organic layers were washed with brine, dried over MgSO₄ and evaporated. Triphenylphosphine oxide was removed by crystallization from ethyl acetate/hexane and the mother liquid was purified by column chromatography on silica gel with hexane:ethyl acetate 3:1 yielding 13.4 g (62%) of (2S,4S)-4-Bromo-1-(naphthalene-2-sulfonyl)-pyrrolidine-2-carboxylic acid benzyl ester as colorless solid, mp 97–98° C., MS: 473 (MH$^+$).

3.38 g (30.1 mmol, 1.1 eq) potassium tert. butylate in 150 ml DMF were treated with 4.4 ml (31.5 mmol, 1.15 eq) 4-methoxybenzyl mercaptane at 0° C. The solution was stirred at RT for 1 h before 12.99 g (27.4 mmol) (2S,4S)-4-Bromo-1-(naphthalene-2-sulfonyl)-pyrrolidine-2-carboxylic acid benzyl ester in 100 ml DMF were added. The reaction was stirred at RT overnight, DMF was removed under vacuum, and the residue redissolved in ethyl acetate and 1M aq. KHSO$_4$. The layers were separated, and the organic one washed with brine, dried over Na$_2$SO$_4$ and evaporated. The crude oil was purified by flash chromatography on silica gel with hexane/ethyl acetate (3:1–2:1) as eluent yielding 7.23 g (48%) (2S,4R)-4-(4-Methoxy-benzylsulfanyl)-1-(naphthalene-2-sulfonyl)-pyrrolidine-2-carboxylic acid benzyl ester as light yellow solid, mp 90–91° C., MS: 547 (M$^+$).

In analogy: (2S,4R)-4-Hydroxy-pyrrolidine-1,2-dicarboxylic acid 1-tert-butyl ester 2-methyl ester with 4-methoxybenzylthiol/potassium tert-butylate gave (2S,4R)-4-(4-Methoxy-benzylsulfanyl)-pyrrolidine-1,2-dicarboxylic acid 1-tert-butyl ester 2-methyl ester, MS: 382 (MH$^+$).

(2S,4R)-4-Hydroxy-1-(naphthalene-2-sulfonyl)-pyrrolidine-2-carboxylic acid methyl ester with 4-methoxybenzylthiol/potassium tert-butylate gave (2S,4R)-4-(4-Methoxy-benzylsulfanyl)-1-(naphthalene-2-sulfonyl)-pyrrolidine-2-carboxylic acid methyl ester as colorless oil, MS: 472 (MH$^+$);

Via chloride: ( (2S,4R)-4-Tritylsulfanyl-pyrrolidine-1,2-dicarboxylic acid 1-tert-butyl ester 2-methyl ester: the synthesis of the intermediate of the present invention is known in the art and described for example in International Patent Application WO 9820001 and European Patent Application Publication No. EP-A-696593.)

A solution of 374 g (1.48 mol) (2S,4R)-4-Hydroxy-pyrrolidine-1,2-dicarboxylic acid 1-tert-butyl ester 2-methyl ester in 1.6 l CH$_2$Cl$_2$ was treated with 680 g (2.6 mol) triphenylphosphine, cooled to 3–5° C. and treated in 10 min with 1.24 l (12.8 mol) CCl$_4$, after 2 h at this temperature cooling was stopped, the reaction temperature raised during 2 h to 35° C. It was cooled down to 20° C. and stirred for further 45 min. After addition of 4 l of n-heptane, the reaction was evaporated to 2.9 l, cooled to 0° C., filtered, the residue was treated twice the same way, the third time by dissolving the residue again in 2 l of CH$_2$Cl$_2$. The solvents were evaporated and filtered through silica gel with hexane/tert.-butyl-methylether 9:1 as eluent. Evaporation of the solvents gave 347 g (89%) of (2S,4S)-4-Chloro-pyrrolidine-1,2-dicarboxylic acid 1-tert-butyl ester 2-methyl ester, MS: 246 (MH$^+$).

A solution of 76 g (0.68 mol) potassium-tert.-butylate in 1.5 l DMF was cooled (−3° C.) and treated slowly (1.5 h) with 202 g (0.73 mol) triphenylmethanethiol in 0.81 DMF (at max 1° C.). After 2.5 h at 0° C., a solution of 161 g (0.61 mol) of (2S,4S)-4-Chloro-pyrrolidine-1,2-dicarboxylic acid 1-tert-butyl ester 2-methyl ester in 0.35 l DMF was added. The reaction was stirred over night at 2° C., evaporated, dissolved in 1.5 l ethyl acetate, poured into 2.7 l aqueous saturated NH$_4$Cl solution and extracted with ethyl acetate (2×). The organic phase was washed with aqueous saturated NaHCO$_3$, dried over Na$_2$SO$_4$ and evaporated. HPLC on silica gel with hexane/ethyl acetate (95:5 to 7:3) gave 268 g (87%) (2S,4R)-4-Tritylsulfanyl-pyrrolidine-1,2-dicarboxylic acid 1-tert-butyl ester 2-methyl ester, MS: 504 (MH$^+$).

Example 2

Hydrolysis (Scheme 1)

To a solution of 14.8 g (31.6 mmol) (2S,4R)-4-(4-Methoxy-benzylsulfanyl)-1-(naphthalene-2-sulfonyl)-pyrrolidine-2-carboxylic acid methyl ester in 950 ml THF were added 950 ml 0.1M LiOH (95 mmol) at 0° C. The solution was stirred at RT for 2 h, diluted with ice water, acidified by the addition of 1M KHSO$_4$ (pH 2), and extracted with ethyl acetate. The combined organic phases were washed with brine, dried over Na$_2$SO$_4$ and were evaporated. The product was crystallized from ethyl acetate/hexane yielding 13.15 g (90%) (2S,4R)-4-(4-Methoxy-benzylsulfanyl)-1-(naphthalene-2-sulfonyl)-pyrrolidine-2-carboxylic acid as colorless solid, MS: 456 (MH$^+$).

Analogously the following compounds were prepared:
(2S,4R)-1-Methanesulfonyl-4-tritylsulfanyl-pyrrolidine-2-carboxylic acid as light brown foam, MS: 466 (M−H$^-$);
(2S,4R)-4-(4-Methoxy-benzylsulfanyl)-pyrrolidine-1,2-dicarboxylic acid 1-tert-butyl ester MS: 366 (M−H$^-$);

Additional compounds were prepared according to the following references: tert-Butyl 2-(isobutyl)hydrazinecarboxylate (Faessler, Alexander; Bold, Guido; Capraro, Hans-Georg; Cozens, Robert; Mestan, Juergen; Poncioni, Bernard; Roesel, Johannes; Tintelnot-Blomley, Marina; Lang, Marc. Aza-Peptide Analogs as Potent Human Immunodeficiency Virus Type-1 Protease Inhibitors with Oral Bioavailability. J. Med. Chem. (1996), 39(16), 3203–3216).

tert-Butyl 2-(methyl)hydrazinecarboxylate (Lenman, Morag M.; Lewis, Arwel; Gani, David. Synthesis of fused 1,2,5-triazepine-1,5-diones and some N2- and N3-substituted derivatives: potential conformational mimetics for cis-peptidyl prolinamides. J. Chem. Soc., Perkin Trans. 1 (1997), Issue 16, 2297–2311).

N-Methyl-hydrazinecarboxylic acid benzyl ester (Lenman, Morag M.; Lewis, Arwel; Gani, David. Synthesis of fused 1,2,5-triazepine-1,5-diones and some N2- and N3-substituted derivatives: potential conformational mimetics for cis-peptidyl prolinamides. J. Chem. Soc., Perkin Trans. 1 (1997), Issue 16, 2297–2311).

Example 3

Synthesis of Hydrazides

Example 3a

Sequence A (Scheme 2)

(step 1) To a solution of 4.4 g (9.6 mmol) (2S,4R)-4-(4-Methoxy-benzylsulfanyl)-1-(naphthalene-2-sulfonyl)-pyrrolidine-2-carboxylic acid in 200 ml CH$_2$Cl$_2$ were added 1.2 g (10.8 mmol,1.1 eq) N-hydroxy-2-pyridone, followed by 2.2 g (10.7 mmol, 1.1 eq) N,N-dicyclohexylcarbodiimide in 25 ml CH$_2$Cl$_2$ at 0° C. over a period of 30 min. The suspension was stirred for additional 4 h at that temperature before 4.2 ml (33.0 mmol, 3.4 eq) NEM and 1.9 g (mmol, 1.05 eq) isobutylhydrazine.sulfate were added. The reaction mixture was stirred at RT over night. The suspension was treated with 0.55 ml (9.6 mmol, 1.0 eq) glacial acetic acid in 10 ml water and stirred for 1.5 h, diluted with aq. NaHCO$_3$ (5%) and extracted with $CH_2Cl_2$. The combined organic phases were washed with 1M $KHSO_4$ solution, water and brine, dried over $Na_2SO_4$ and evaporated. Tituration with hexane yields 5.02 g (quant) (2S,4R)-4-(4-Methoxy -benzylsulfanyl)-1-(naphthalene-2-sulfonyl)-pyrrolidine-2-carboxylic acid N'-isobutyl-hydrazide, which was directly subjected to the following reaction.

b) benzylhydrazine followed by deprotection: (2S,4R)-4-Mercapto-1-(naphthalene-2-sulfonyl)-pyrrolidine-2-carboxylic acid N'-benzyl-hydrazide as white solid, MS: 442 (MH$^+$);

c) p-toluenesulfonylhydrazine followed by deprotection: (2S,4R)-4-Mercapto-1-(naphthalene-2-sulfonyl)-

Scheme 2

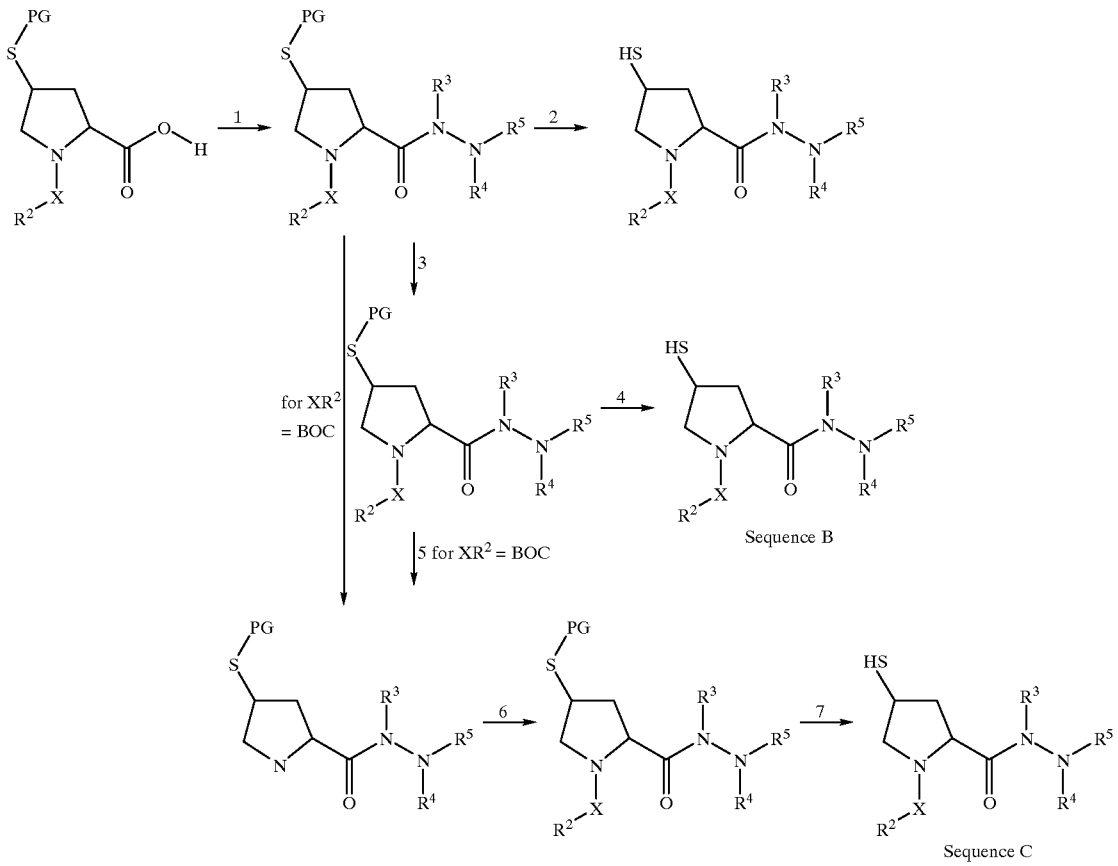

1. N-hydroxy-2-pyridone, N, N-dicyclohexylcarbodiimide, 4-Ethylmorpholine and NHR$^3$NHR$^4$ in $CH_2Cl_2$
2. Triethylsilane in TFA
3. N-Ethyldiisopropylamine and R$^{5'}$SO$_2$Cl/DMAP in $CH_2Cl_2$
4. Triethylsilane in TFA and Acetonitrile or $CH_2Cl_2$
5. TFA, $CH_2Cl_2$
6. R$^2$Xchloride, $CH_2Cl_2$, NEM or Huenig's Base
7. Triethylsilane in TFA (step 2) 222 mg (0.42 mmol) (2S,4R)-4-(4-Methoxy-benzylsulfanyl)-1-(naphthalene-2-sulfonyl)-pyrrolidine-2-carboxylic acid N'-isobutyl-hydrazide in 10 ml TFA were treated with 0.68 ml (4.2 mmol, 10 eq) triethylsilane at 80° C. for 90 min. The solvent was evaporated in vacuo and the crude product was purified by flash chromatography yielding 148 mg (86%) (2S,4R)-4-Mercapto-1-(naphthalene-2-sulfonyl)-pyrrolidine-2-carboxylic acid N'-isobutyl hydrazide as light yellow crystalline, MS: 408 (MH$^+$).

Analogously the following compounds were prepared:

From (2S,4R)-4-(4-Methoxy-benzylsulfanyl)-1-(naphthalene-2-sulfonyl)-pyrrolidine-2-carboxylic acid and pyrrolidine-2-carboxylic acid N'-(4-methyl-benzenesulfonyl)-hydrazide as white solid, MS: 506 (MH$^+$);

d) methylhydrazine followed by deprotection: (2S,4R)-4-Mercapto-1-(naphthalene-2-sulfonyl)-pyrrolidine-2-carboxylic acid N'-methyl-hydrazide as white crystalline, MS: 366 (MH$^+$);

From (2S,4R)-1-Methanesulfonyl-4-tritylsulfanyl-pyrrolidine-2-carboxylic acid and p-toluenesulfonylhydrazine followed by deprotection: (2S,4R)-4-Mercapto-1-methanesulfonyl -pyrrolidine-2-carboxylic acid N'-(4-methyl-benzenesulfonyl)-hydrazide as white crystalline, MS: 394 (MH$^+$);

Example 3b

Sequence B (Step 1 from Sequence A Followed by Step 3,4- Scheme 2)

(step 3) 4.3 g (3.15 mmol) (2S,4R)-4-(4-Methoxy-benzylsulfanyl)-1-(naphthalene-2-sulfonyl)-pyrrolidine-2-carboxylic acid N'-isobutyl-hydrazide in 450 ml $CH_2Cl_2$ were treated with 5.6 ml (32.6 mmol, 4 eq) N-ethyldiisopropylamine, 3.1 g (16.3 mmol, 2 eq) p-toluene sulfonyl chloride and 100 mg (0.8 mmol, 0.1 eq) DMAP at 0° C. and was stirred at RT over night. 2.05 g (16.1 mmol, 2 eq) $MeNHCH_2CO_2K$ were added and, the solution was stirred at RT for 1 h, 1M $KHSO_4$ solution was added and, the phases were separated. The organic layer was extracted with sat. $NaHCO_3$ and, the inorganic layers were washed with $CH_2Cl_2$. The combined organic phases were washed with brine, dried over $Na_2SO_4$ and evaporated. Purification of the crude residue by flash chromatography with hexane:ethyl acetate 2:1 as eluent yields 2.68 g (48%) (2S,4R)-4-(4-Methoxy-benzylsulfanyl)-1-(naphthalene-2-sulfonyl)-pyrrolidine-2-carboxylic acid N'-isobutyl-N'-(4-methyl-benzenesulfonyl)-hydrazide, which was directly subjected to the following reaction.

(step 4) To 2.68 g (3.9 mmol, 1 eq) (2S,4R)-4-(4-Methoxy-benzylsulfanyl)-1-(naphthalene-2-sulfonyl)-pyrrolidine-2-carboxylic acid N'-isobutyl-N'-(4-methyl-benzenesulfonyl)-hydrazide in 100 ml TFA were added 6.2 ml (39 mmol, 10 eq) triethylsilane and the mixture was heated to 80° C. for 1.5 h, concentrated in vacuo and redissolved in toluene and evaporated. Titration with hexane yields the crude product which was further purified by flash chromatography with hexane:ethyl acetate 1:1 yielding 1.65 g (74%)(2S,4R)-4-Mercapto-1-(naphthalene-2-sulfonyl)-pyrrolidine-2-carboxylic acid N'-isobutyl-N'-(4-methyl-benzenesulfonyl)-hydrazide as white crystalline, MS: 562 ($MH^+$).

Analogously, the following compounds were prepared (steps 1,3,4):

From (2S,4R)-4-(4-Methoxy-benzylsulfanyl)-1-(naphthalene-2-sulfonyl)-pyrrolidine-2-carboxylic acid b) and methylhydrazine, followed by reaction with p-toluenesulfonyl chloride and deprotection: (2S,4R)-4-Mercapto-1-(naphthalene-2-sulfonyl)-pyrrolidine-2-carboxylic acid N'-methyl-N'-(4-methyl-phenylsulfonyl)-hydrazide as white crystalline, MS: 520 ($MH^+$);

c) and isobutylhydrazine-sulfate, followed by reaction with 4-t-butyl-phenylsulfonyl chloride and deprotection: (2S,4R)-4-Mercapto-1-(naphthalene-2-sulfonyl)-pyrrolidine-2-carboxylic acid N'-(4-tert-butyl-benzenesulfonyl)-N'-isobutyl-hydrazide as white crystalline, MS: 604 ($MH^+$);

d) and methylhydrazine, followed by reaction with methanesulfonyl chloride and deprotection: (2S,4R)-4-Mercapto-1-(naphthalene-2-sulfonyl)-pyrrolidine-2-carboxylic acid N'-methanesulfonyl-N'-methyl-hydrazide as white solid, MS: 444 ($MH^+$);

e) and isobutylhydrazine-sulfate, followed by reaction with methanesulfonyl chloride and deprotection: (2S,4R)-4-Mercapto-1-(naphthalene-2-sulfonyl)-pyrrolidine-2-carboxylic acid N'-isobutyl-N'-methanesulfonyl-hydrazide as white crystalline, MS: 486 ($MH^+$);

f) and benzylhydrazine, followed by reaction with methanesulfonyl chloride and deprotection: (2S,4R)-4-Mercapto-1-(naphthalene-2-sulfonyl)-pyrrolidine-2-carboxylic acid N'-benzyl-N'-methanesulfonyl-hydrazide as white crystalline, MS: 520 ($MH^+$);

g) and benzylhydrazine, followed by reaction with p-toluenesulfonyl chloride and deprotection: (2S,4R)-4-Mercapto-1-(naphthalene-2-sulfonyl)-pyrrolidine-2-carboxylic acid N'-benzyl-N'-(4-methyl-phenylsulfonyl)-hydrazide as white crystalline, MS: 596 ($MH^+$);

From (2S,4R)-1-Methanesulfonyl-4-tritylsulfanyl-pyrrolidine-2-carboxylic acid a2) and benzylhydrazine, followed by reaction with methanesulfonyl chloride and deprotection: (2S,4R)-4-Mercapto-1-methanesulfonyl-pyrrolidine-2-carboxylic acid N'-benzyl-N'-methanesulfonyl-hydrazide as white solid, MS: 408 ($MH^+$);

b2) and isobutylhydrazine-sulfate, followed by reaction with methanesulfonyl chloride and deprotection: (2S,4R)-4-Mercapto-1-methanesulfonyl-pyrrolidine-2-carboxylic acid N'-isobutyl-N'-methanesulfonyl-hydrazide as colorless solid, MS: 450 ($MH^+$);

c2) and isobutylhydrazine-sulfate, followed by reaction with p-toluenesulfonyl chloride and deprotection: (2S,4R)-4-Mercapto-1-methanesulfonyl-pyrrolidine-2-carboxylic acid N'-isobutyl-N'-(4-methyl-benzenesulfonyl)-hydrazide as colorless solid, MS: 374 ($MH^+$);

d2) and isobutylhydrazine-sulfate, followed by reaction with 4-tert-butyl-benzenesulfonyl chloride and deprotection: (2S,4R)-4-Mercapto-1-methanesulfonyl-pyrrolidine-2-carboxylic acid N'-(4-tert-butyl-benzenesulfonyl)-N'-isobutyl-hydrazide as white crystalline, MS: 492 ($MH^+$);

Example 3c

Sequence C (Scheme 2)

Analogously to sequence A,B (steps 1,3), from (2S,4R)-4-(4-Methoxy-benzylsulfanyl)-pyrrolidine-1,2-dicarboxylic acid 1-tert-butyl ester and methylhydrazine, followed by treatment with p-toluenesulfonyl chloride (2S,4R)-2-[N'-Methyl-N'-(4-methyl-phenylsulfonyl)-hydrazinocarbonyl]-4-(4-methoxy-benzylsulfanyl)-pyrrolidine-1-carboxylic acid 1-tert-butyl ester, which was directly subjected to the following reaction.

(step 5) 2.37 g (4.3 mmol) (2S,4R)-2-[N'-Methyl-N'-(4-methyl-phenylsulfonyl)-hydrazinocarbonyl]-4-(4-methoxy-benzylsulfanyl)-pyrrolidine-1-carboxylic acid 1-tert-butyl ester in 10 ml $CH_2Cl_2$ were treated with 4 ml TFA at 0° C. and kept in the freezer over night. The solvent was evaporated, the crude material was dissolved and evaporated with toluene (2x) and hexane (3x) yielding (2S,4R)-2-[N'-Methyl-N'-(4-methyl-phenylsulfonyl)-hydrazinocarbonyl]-4-(4-methoxy-benzylsulfanyl)-pyrrolidine as TFA salt as crude product, which was subjected to the following reaction without further purification.

(step 6) To 250 mg (0.44 mmmol, 1.0 eq) (2S,4R)-2-[N'-Methyl-N'-(4-methyl-phenylsulfonyl)-hydrazinocarbonyl]-4-(4-methoxy-benzylsulfanyl)-pyrrolidine.TFA in 5 ml $CH_2Cl_2$ were added 360 µl (2.1 mmol, 4.8 eq) N-ethyldiisopropylamine and 70 µl (0.56 mmol, 1.2 eq) phenyl chloroformate at 0° C. The solution was stirred at RT over night, 1N $KHSO_4$ was added, the phases were separated and the inorganic one was extracted with $CH_2Cl_2$, the organic layer was washed with 1M $KHSO_4$ and brine, dried over $Na_2SO_4$ and evaporated.

(step 7) The crude material was redissolved in 10 ml TFA and, 700 µl (4.4 mmol, 10 eq) triethylsilane were added at RT and the solution was stirred at 80° C. for 70 min. Evaporation and flash chromatography with hexane:ethyl acetate 1:1 followed by lyophilisation yields 149.2 mg (75%) (2S,4R)-2-[N'-Methyl-N'-(4-methyl-phenylsulfonyl)-hydrazinocarbonyl]-4-mercapto-pyrrolidine-1-carboxylic acid phenyl ester as white solid, MS: 450 ($MH^+$).

In a similar manner (step 6,7) the following compounds were prepared: from (2S,4R)-2-[N'-Methyl-N'-(4-methyl-phenylsulfonyl)-hydrazinocarbonyl]-4-(4-methoxy-benzylsulfanyl)-pyrrolidine.TFA with n-butyl chloroformate, i-propyl chloroformate, butylsulfamoyl chloride, cyclopropylsulfamoylchloride, benzylsulfamoyl-chloride:

(2S,4R)-2-[N'-Methyl-N'-(4-methyl-phenylsulfonyl)-hydrazinocarbonyl]-4-mercapto -pyrrolidine-1-carboxylic acid butyl ester as colorless gum, MS: 430 (MH$^+$);

(2S,4R)-2-[N'-Methyl-N'-($^4$-methyl-phenylsulfonyl)-hydrazinocarbonyl]-4-mercapto-pyrrolidine-1-carboxylic acid isopropyl ester as white solid, MS: 416 (MH$^+$);

(2S,4R)-2-[N'-Methyl-N'-(4-methyl-phenylsulfonyl)-hydrazinocarbonyl]-4-mercapto-pyrrolidine-1-sulfonic acid butylamide as white lyoph solid, MS: 463 (M–H)$^-$;

(2S,4R)-2-[N'-Methyl-N'-(4-methyl-phenylsulfonyl)-hydrazinocarbonyl]-4-mercapto-pyrrolidine-1-sulfonic acid cyclopropylamide as white lyoph solid, MS: 447 (M–H)$^-$;

(2S,4R)-2-[N'-Methyl-N'-($^4$-methyl-phenylsulfonyl)-hydrazinocarbonyl]-4-mercapto-pyrrolidine-1-sulfonic acid benzylamide as white lyoph solid, MS: 497 (M–H)$^-$;

From (2S,4R)-2-[N'-Isobutyl-N'-(4-methyl-phenylsulfonyl)-hydrazinocarbonyl]-4-(4-methoxy-benzylsulfanyl)-pyrrolidine-1-carboxylic acid 1-tert-butyl ester was treated with i-propyl chloroformate, n-butyl chloroformate, benzyl chloroformate, phenyl chloroformate, quinoline-8-sulfonyl chloride, thiophene-2-sulfonyl chloride, benzylsulfamoylchloride, butylsulfamoyl chloride or cyclopropylsulfamoylchloride according to protocols (steps 5–7) to give the following compounds:

(2S,4R)-2-[N'-Isobutyl-N'-(4-methyl-phenylsulfonyl)-hydrazinocarbonyl]-4-mercapto-pyrrolidine-1-carboxylic acid isopropyl ester as white solid, MS: 458 (MH$^+$);

(2S,4R)-2-[N'-Isobutyl-N'-(4-methyl-phenylsulfonyl)-hydrazinocarbonyl]-4-mercapto-pyrrolidine-1-carboxylic acid butyl ester as white solid, MS: 472 (MH$^+$);

(2S,4R)-2-[N'-Isobutyl-N'-(4-methyl-phenylsulfonyl)-hydrazinocarbonyl]-4-mercapto-pyrrolidine-1-carboxylic acid benzyl ester as white solid, MS: 506 (MH$^+$);

(2S,4R)-2-[N'-Isobutyl-N'-(4-methyl-phenylsulfonyl)-hydrazinocarbonyl]-4-mercapto-pyrrolidine-1-carboxylic acid phenyl ester as white solid, MS: 492 (MH$^+$);

(2S,4R)-4-Mercapto-1-(quinoline-8-sulfonyl)-pyrrolidine-2-carboxylic acid N'-isobutyl-N'-(4-methyl-benzyl)-hydrazide as white solid, MS: 563 (MH$^+$);

(2S,4R)-4-Mercapto-1-(thiophen-2-sulfonyl)-pyrrolidine-2-carboxylic acid N'-isobutyl-N'-(4-methyl-benzyl)-hydrazide as white solid, MS: 518 (MH$^+$);

(2S,4R)-2-[N'-Isobutyl-N'-(4-methyl-phenylsulfonyl)-hydrazinocarbonyl]-4-mercapto-pyrrolidine-1-sulfonic acid benzylamide as white lyoph solid, mp 67° C. MS: 539 (M–H)$^-$;

(2S,4R)-2-[N'-Isobutyl-N'-(4-methyl-phenylsulfonyl)-hydrazinocarbonyl]-4-mercapto-pyrrolidine-1-sulfonic acid butylamide as white lyoph solid, MS: 467 (M–H)$^-$;

(2S,4R)-2-[N'-Isobutyl-N'-(4-methyl-phenylsulfonyl)-hydrazinocarbonyl]-4-mercapto-pyrrolidine-1-sulfonic acid cyclopropylamide as white lyoph solid, MS: 489 (M–H)$^-$.

Example 3d

Sequence D—Direct Formation from the Ester (Scheme 3)

Analogously to Ruye Xing and Robert P. Hanzlik, J. Med. Chem. 1998, 41, 1344–1351 the following reactions were carried out:

(step 8) To a solution of 5 g (10.6 mmol, 1 eq) (2S,4R)-4-(4-Methoxy-benzylsulfanyl)-1-(naphthalene-2-sulfonyl)-pyrrolidine-2-carboxylic acid methyl ester in 20 ml methanol were added 6.45 ml (110 mmol, 10 eq) hydrazine-hydrate and the solution was stirred at RT for 3 days. The solvent was evaporated, followed by solving and evaporating with EtOH, ether and hexane. The light yellow solid was dried in vacuo giving (2S,4R)-4-(4-Methoxy-benzylsulfanyl)-1-(naphthalene-2-sulfonyl)-pyrrolidine-2-carboxylic acid hydrazide, mp 130° C., MS: 472 (MH$^+$).

(step 9) 150 mg (0.3 mmol, 1.0 eq) (2S,4R)-4-(4-Methoxy-benzylsulfanyl)-1-(naphthalene-2-sulfonyl)-pyrrolidine-2-carboxylic acid hydrazide in 5 ml TFA and 0.65 ml triisopropylsilane were stirred for 3 d at RT. The solvent was evaporated and the residue redissolved in sat. NaHCO$_3$ solution:ethyl acetate, the phases were separated and the inorganic one was extracted with ethyl acetate. The combined organic phases were washed with water and brine. Column chromatography yields 68 mg ( 61%) (2S,4R)-4-Mercapto-1-(naphthalene-2-sulfonyl)-pyrrolidine-2-carboxylic acid hydrazide as white foam, MS: 352 (MH$^+$).

Scheme 3

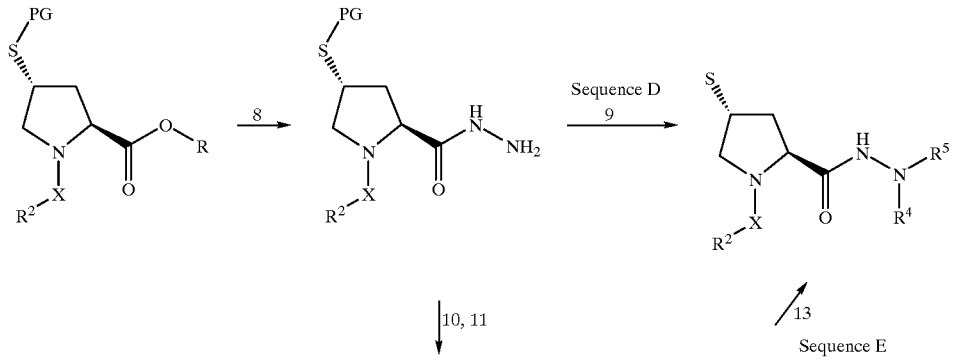

-continued

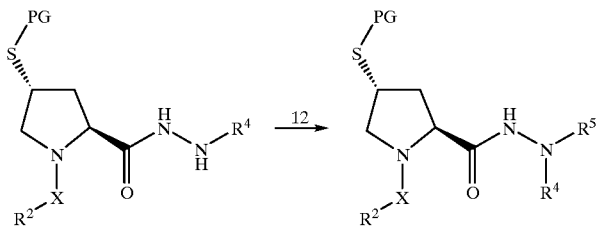

8. NH$_2$NH$_2$ H$_2$O in EtOH
9. Triisopropylsilane in TFA
10. RCHO, EtOH
11. NaBH$_3$CN, THF
12. R$^5$-SO$_2$Cl, DMAP, CH$_2$Cl$_2$, NEM or Hunig's Base
13. triethylsilane in TFA and Acetonitrile or CH$_2$Cl$_2$ Example 3e Sequence E—intermediates (Scheme 3)

Analogously to Sequence D step 8, the following compound was prepared from (2S,4R)-1-(Naphthalene-2-sulfonyl)-4-tritylsulfanyl-pyrrolidine-2-carboxylic acid methyl ester and hydrazine hydrate:
(2S,4R)-1-(Naphthalene-2-sulfonyl)-4-tritylsulfanyl-pyrrolidine-2-carboxylic acid hydrazide as off-white solid, mp 172° C., MS: 594 (MH$^+$).

(step 10) To a suspension of 3.0 g (5.05 mmol) (2S,4R)-1-(Naphthalene-2-sulfonyl)-4-tritylsulfanyl-pyrrolidine-2-carboxylic acid hydrazide in ethanol were added 0.56 ml (5.6 mmol, 1.1 eq) benzaldehyde at RT, and the reaction mixture was heated to 80° C. for 3 h. The solvent was evaporated and the residue was purified by flash chromatography on silica gel with ethyl acetate:hexane 1:1 as eluent yielding 2.75 g (80%) (2S,4R)-1-(Naphthalene-2-sulfonyl)-4-tritylsulfanyl-pyrrolidine-2-carboxylic acid benzylidene-hydrazide as white foam, MS: 682 (MH$^+$).

(step 11) To 2.48 g (3.64 mmol) (2S,4R)-1-(Naphthalene-2-sulfonyl)-4-tritylsulfanyl-pyrrolidine-2-carboxylic acid benzylidene-hydrazide were added 228.6 mg (3.64 mmol, 1.0 eq) NaBH$_3$CN in 12.4 ml THF, followed by 691.8 mg (3.64 mmol, 1.0 eq) toluene-4-sulfonic acid in 8.7 ml THF. The solution was stirred at RT for 2 h, additional mmol,0.3 eq) NaBH$_3$CN were added, and the reaction was stirred overnight at RT. The mixture was diluted with ethyl acetate and washed with brine, sat. NaHCO$_3$ solution and brine, dried over Na$_2$SO$_4$ and the solvent was evaporated.

The residue was dissolved in 11 ml 1M NaOH and 15 ml THF and stirred for 1 h, diluted with ethyl acetate and 9 ml 1M KHSO$_4$ were added, followed by 5% NaHCO$_3$ solution. The slightly basic solution was extracted with ethyl acetate. The organic phase was washed with water and brine, dried over Na$_2$SO$_4$ and evaporated yielding 2.45 g (98%) (2S,4R)-1-(Naphthalene-2-sulfonyl)-4-tritylsulfanyl-pyrrolidine-2-carboxylic acid N'-benzyl-hydrazide as white foam, MS: 684 (MH$^+$). (analogously to Alexander Fässler, Guido Bold, Hans-Georg Capraro, Robert Cozens, Jürgen Mestan, Bernard Poncioni, Johannes Rösel, Marina Tintelnot-Blomley, and Marc Lang, J. Med. Chem. 1996, 39, 16, 3203–3216.)

Analogously, the following compound was prepared from (2S,4R)-1-(Naphthalene-2-sulfonyl)-4-tritylsulfanyl-pyrrolidine-2-carboxylic acid hydrazide and 2,5-difluoro-benzaldehyde:
(2S,4R)-1-(Naphthalene-2-sulfonyl)-4-tritylsulfanyl-pyrrolidine-2-carboxylic acid N'-(2,5-difluoro-benzyl)-hydrazide as white foam, MS: 720 (MH$^+$).

Example 3e

Sequence E—final Products (Scheme 3)

(step 12) To 200 mg (0.3 mmol) (2S,4R)-1-(Naphthalene-2-sulfonyl)-4-tritylsulfanyl-pyrrolidine-2-carboxylic acid N'-benzyl-hydrazide in 3 ml CH$_2$Cl$_2$ were added 60 μl (0.35 mmol, 1.2 eq) N,N-diisopropylethylamine, 72.5 mg (0.35 mmol, 1.2 eq) 4-methoxybenzene sulfonylchloride and 22.5 mg (0.12 eq) DMAP-poly at 0° C. The suspension was shaken at RT for 3 days, additional 25 μl (0.15 mmol, 0.5 eq) N,N-diisopropylethylamine, 31 mg (0.15 mmol, 0.5 eq) 4-methoxybenzene sulfonylchloride and 22.5 mg (0.12 eq) DMAP-poly were added and the reaction was continued for a day. After filtration and washing of the resin with CH$_2$Cl$_2$, the organic phase was concentrated and the crude material purified by flash chromatography yielding 152 mg (61%) (2S,4R)-1-(Naphthalene-2-sulfonyl)-4-tritylsulfanyl-pyrrolidine-2-carboxylic acid N'-benzyl-N'-(4-methoxy-benzenesulfonyl)-hydrazide which was directly subjected to the following reaction.

(step 13) To 148 mg (0.17 mmol) ) (2S,4R)-1-(Naphthalene-2-sulfonyl)-4-tritylsulfanyl-pyrrolidine-2-carboxylic acid N'-benzyl-N'-(4-methoxy-benzenesulfonyl)-hydrazide in 3.0 ml TFA were added 276 μl (1.73 mmol, 10 eq) triethylsilane at 0° C. The mixture was stirred at RT for 30 min, the solvent was evaporated and the residue was redissolved in ethyl acetate, sat. aq. NaHCO$_3$ solution, the layers were separated and the inorganic one extracted with ethyl acetate. The combined organic layers were washed with brine, dried over Na$_2$SO$_4$ and evaporated. The residue was purified by flash chromatography with a gradient of ethyl acetate:hexane (1:1.5 to 1:1) yielding 76 mg (72%) (2S,4R)-4-Mercapto-1-(naphthalene-2-sulfonyl)-pyrrolidine-2-carboxylic acid N'-benzyl-N'-(4-methoxy-benzenesulfonyl)-hydrazide as white foam, MS: 612 (MH$^+$).

Analogously, the following compounds were prepared from (2S,4R)-1-(Naphthalene -2-sulfonyl)-4-tritylsulfanyl-pyrrolidine-2-carboxylic acid N'-benzyl-hydrazide and p-toluoyl chloride, acetyl chloride, p-anisoyl chloride followed by deprotection:
(b) (2S,4R)-4-Methyl-benzoic acid N-benzyl-N'-[4-mercapto-1-(naphthalene-2-sulfonyl)-pyrrolidine-2-carbonyl]-hydrazide as white foam, MS: 560 (MH$^+$).
(c) (2S,4R)-4-Mercapto-1-( naphthalene-2-sulfonyl)-pyrrolidine-2-carboxylic acid N'-acetyl-N'-benzyl-hydrazide as white solid, mp 64° C., MS: 484 (MH$^+$).
(d) (2S,4R)-4-Methoxy-benzoic acid N-benzyl-N'-[4-mercapto-1-(naphthalene-2-sulfonyl)-pyrrolidine-2-carbonyl]-hydrazide as white foam, MS: 576 (MH$^+$).

From (2S,4R)-1-(Naphthalene-2-sulfonyl)-4-tritylsulfanyl-pyrrolidine-2-carboxylic acid N'-(2,5-difluoro-benzyl)-hydrazide and 2,4-difluorobenzoyl chloride, 2-thiophene carbonyl chloride, methanesulfonyl chloride, methoxybenzenesulfonyl chloride, 2-thiophenesulfonyl chloride, benzenesulfonyl chloride, 4-fluorobenzenesulfonyl chloride:

(e) (2S,4R)-2,4-Difluoro-benzoic acid N-(2,5-difluoro-benzyl)-N'-[4-mercapto-1-(naphthalene-2-sulfonyl)-pyrrolidine-2-carbonyl]-hydrazide as white foam, MS: 618 (MH$^+$).

(f) (2S,4R)-Thiophene-2-carboxylic acid N-(2,5-difluoro-benzyl)-N'-[4-mercapto-1-(naphthalene-2-sulfonyl)-pyrrolidine-2-carbonyl]-hydrazide as white foam, MS: 588 (MH$^+$).

(g) (2S,4R)-1-(Naphthalene-2-sulfonyl)-4-tritylsulfanyl-pyrrolidine-2-carboxylic acid N'-(2,5-difluoro-benzyl)-N'-methanesulfonyl-hydrazide as white foam, MS: 556 (MH$^+$).

(h) (2S,4R)-1-(Naphthalene-2-sulfonyl)-4-tritylsulfanyl-pyrrolidine-2-carboxylic acid N'-(2,5-difluoro-benzyl)-N'-(4-methoxy-benzenesulfonyl)-hydrazide as white foam, MS: 648 (MH$^+$).

(i) (2S,4R)-1-(Naphthalene-2-sulfonyl)-4-tritylsulfanyl-pyrrolidine-2-carboxylic acid N'-(2,5-difluoro-benzyl)-N'-(thiophene-2-sulfonyl)-hydrazide as white foam, MS: 624 (MH$^+$).

(j) (2S,4R)-1-(Naphthalene-2-sulfonyl)-4-tritylsulfanyl-pyrrolidine-2-carboxylic acid N'-(2,5-difluoro-benzyl)-N'-benzenesulfonyl-hydrazide as white foam, MS: 618 (MH$^+$).

(k) (2S,4R)-1-(Naphthalene-2-sulfonyl)-4-tritylsulfanyl-pyrrolidine-2-carboxylic acid N'-(2,5-difluoro-benzyl)-N'-(4-fluoro-benzenesulfonyl)-hydrazide as white foam, MS: 636 (MH$^+$).

Example 3f

Synthesis According to Scheme 4

Analogously to Sequence A -step 1, from (2S,4R)-4-(4-Methoxy-benzylsulfanyl)-1-(naphthalene-2-sulfonyl)-pyrrolidine-2-carboxylic acid and N-Methyl-hydrazinecarboxylic acid benzyl ester was prepared intermediate (2S,4R)-N'-[4-(4-Methoxy-benzylsulfanyl)-1-(naphthalene-2-sulfonyl)-pyrrolidine-2-carbonyl]-N-methyl-hydrazinecarboxylic acid benzyl ester as off-white crystalline, MS: 620 (MH$^+$).

(step 14) 2.45 g (1.52 mmol) (2S,4R)-N'-[4-(4-Methoxy-benzylsulfanyl)-1-(naphthalene-2-sulfonyl)-pyrrolidine-2-carbonyl]-N-methyl-hydrazinecarboxylic acid benzyl ester were dissolved in 9 ml acetic acid and 9 ml HBr (33% in acetic acid) were added at 0° C. stirred for 4 h at 0° C. The solution was concentrated and the residue was dissolved in CH$_2$Cl$_2$ and sat. aq NaHCO$_3$ solution, the layers were separated and the inorganic one was extracted with CH$_2$Cl$_2$ and the combined organic phases were washed with brine and dried over Na$_2$SO$_4$. The crude product was purified by flash chromatography with ethyl acetate:hexane 1:1 yielding 380 mg (44%) (2S,4R)-4-(4-Methoxy-benzylsulfanyl)-1-(naphthalene-2-sulfonyl)-pyrrolidine-2-carboxylic acid N-benzyl-N-methyl-hydrazide as white solid, mp 83.2° C., MS: 576 (MH$^+$).

Deprotection according to Scheme 2 (step 4) gave:
(2S,4R)4-Mercapto-1-(naphthalene-2-sulfonyl)-pyrrolidine-2-carboxylic acid N-benzyl-N-methyl-hydrazide as white solid, mp 69° C., MS: 456 (MH$^+$).

(step 16) 180 mg (0.31 mmol) (2S,4R)-4-(4-Methoxy-benzylsulfanyl)-1-(naphthalene-2-sulfonyl)-pyrrolidine-2-carboxylic acid N-benzyl-N-methyl-hydrazide in 7.5 ml DMF were treated with 16.5 mg (0.34 mmol, 1.1 eq) NaH and 21 μl (0.34 mmol, 1.1 eq) methyl iodide at 0° C. and, the solution was stirred for 3 h at RT. The solution was diluted with water and CH$_2$Cl$_2$. The phases were separated and the inorganic layer was extracted with CH$_2$Cl$_2$, the combined organic layers were washed with brine, dried over Na$_2$SO$_4$ and were evaporated. The crude material was purified by flash chromatography with a gradient of ethyl acetate:hexane 2:1 to ethyl acetate yielding 110 mg (60%) (2S,4R)-4-(4-Methoxy-benzylsulfanyl)-1-(naphthalene-2-sulfonyl)-pyrrolidine-2-carboxylic acid N'-benzyl-N,N-dimethyl-hydrazide which was deprotected using the protocol described Scheme 4:

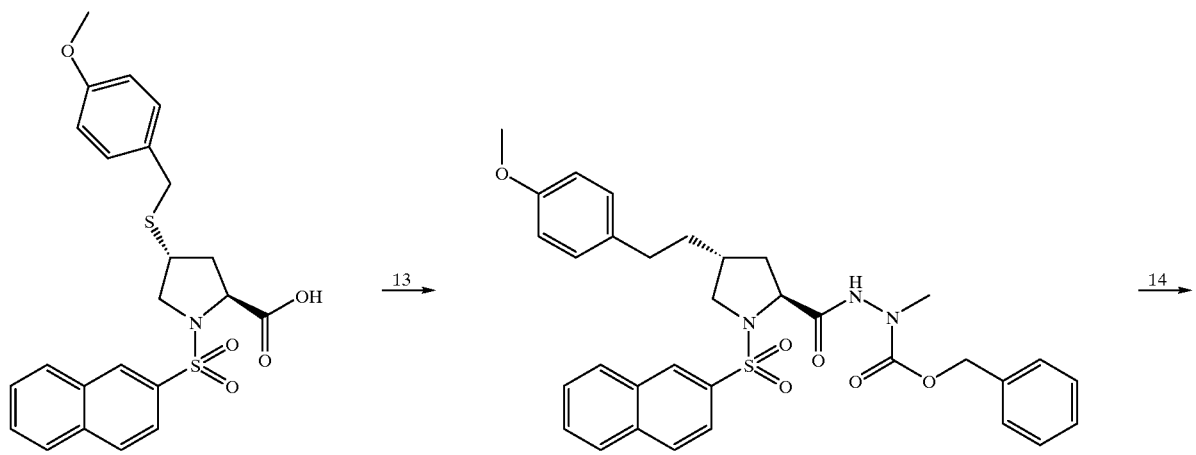

-continued

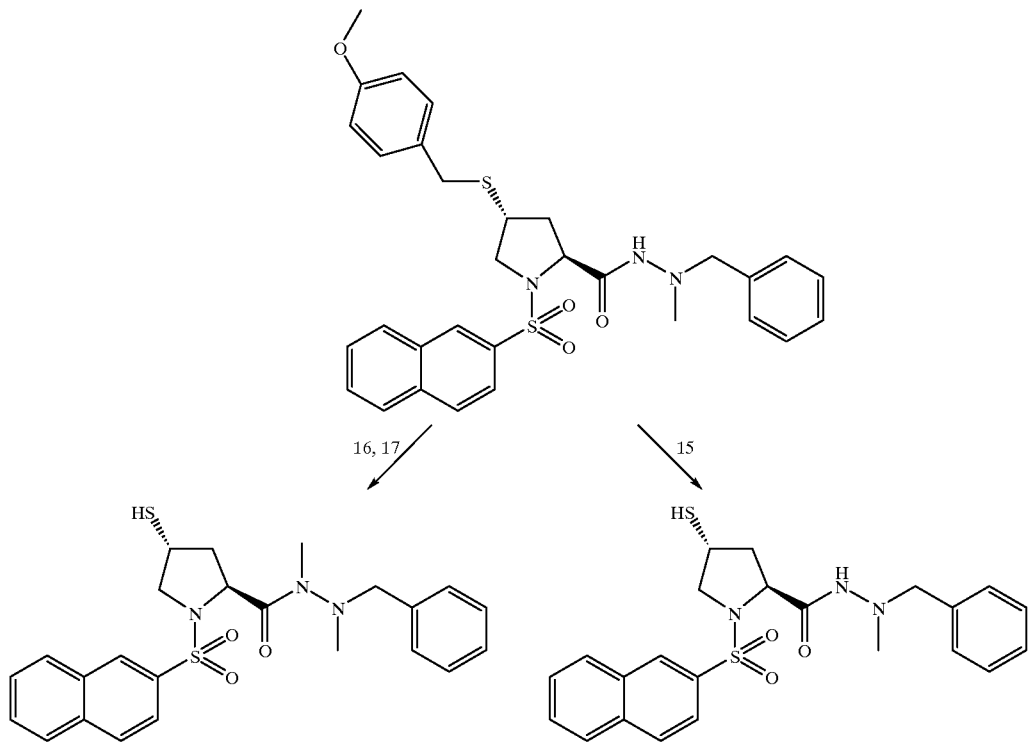

13) N-Methyl-hydrazinecarboxylic acid benzyl ester, N-Hydroxy-2-pryridone, DDC, NEM, CH$_2$Cl$_2$
14) HBr, AcOH
15) TFA, Et$_3$SiH
16) NaH, RBr, DMF
17) TFA, Et$_3$, SiH for Scheme 2 (step 4) to give (2S,4R)-4-Mercapto-1-(naphthalene-2-sulfonyl)-pyrrolidine-2-carboxylic acid N'-benzyl-N,N-dimethyl-hydrazide as white solid, mp 133.2° C., MS: 470 (MH$^+$).

Example 3g

Synthesis According to Scheme 5

Analogously to Sequence A -step 1, from (2S,4R)-4-(4-Methoxy-benzylsulfanyl)-1-(naphthalene-2-sulfonyl)-pyrrolidine-2-carboxylic acid and tert-Butyl 2-(methyl) hydrazinecarboxylate was prepared intermediate (2S,4R)-N'-[4-(4-Methoxy-benzylsulfanyl)-1-( naphthalene-2-sulfonyl)-pyrrolidine-2-carbonyl]-N'-methyl-hydrazinecarboxylic acid tert-butyl ester as white crystalline, MS: 586 (MH$^+$).

(step 19) To 200 mg (0.34 mmol) (2S,4R)-N'-[4-(4-Methoxy-benzylsulfanyl)-1-(naphthalene-2-sulfonyl)-pyrrolidine-2-carbonyl]-N'-methyl-hydrazinecarboxylic acid tert-butyl ester in 10 ml TFA were added 0.54 ml (3.4 mmol, 10 eq) triethylsilane at RT and the solution was stirred at 80° C. for 1 h. The solvent was evaporated in vacuo and the crude material was purified by flash chromatography with ethyl acetate/hexane yielding 61.6 mg (40%) (2S,4R)-4-Mercapto-1-(naphthalene-2-sulfonyl)-pyrrolidine-2-carboxylic acid N-methyl-N'-trifluoroacetyl-hydrazide as white solid, MS: 461 (MH$^+$).

(step 20, 21) According to the procedure (Scheme 4, step 16) was prepared from (2S,4R)-N'-[4-(4-Methoxy-benzylsulfanyl)-1-(naphthalene-2-sulfonyl)-pyrrolidine-2-carbonyl]-N'-methyl-hydrazinecarboxylic acid tert-butyl ester and benzyl bromide (2S,4R)-N'-[4-(4-Methoxy-benzylsulfanyl)-1-(naphthalene-2-sulfonyl)-pyrrolidine-2-carbonyl]-N'-methyl-N-benzyl-hydrazinecarboxylic acid tert-butyl ester which was directly BOC and PMB-deprotected according to Scheme 2 (step 4) to give (2S,4R)-4-Mercapto-1-(naphthalene-2-sulfonyl)-pyrrolidine-2-carboxylic acid N-benzyl-N-methyl-hydrazide as colorless oil, mp, MS: 456 (MH$^+$).

(Step 22) 2 g (3.4 mmol) (2S,4R)-N'-[4-(4-Methoxy-benzylsulfanyl)-1-(naphthalene-2-sulfonyl)-pyrrolidine-2-carbonyl]-N'-methyl-hydrazinecarboxylic acid tert-butyl ester in 9 ml CH$_2$Cl$_2$ were treated with 3.4 ml TFA for 2 h. The solution was concentrated, redissolved in toluene and evaporated. The residue was dissolved in ethyl acetate and sat. aq. NaHCO$_3$, the layers were separated and the inorganic one was extracted with ethyl acetate, the combined organic ones were washed wit brine, dried over Na$_2$SO$_4$ and concentrated yielding 1.67 g (quant) (2S,4R)-4-(4-Methoxy-benzylsulfanyl)-1-(naphthalene-2-sulfonyl)-pyrrolidine-2-carboxylic acid N-methyl-hydrazide as white solid, MS: 486 (MH$^+$).

(Step 23) To 1.67 g (3.4 mmol) (2S,4R)-4-(4-Methoxy-benzylsulfanyl)-1-(naphthalene-2-sulfonyl)-pyrrolidine-2-carboxylic acid N-methyl-hydrazide were added 0.78 g (4.08 mmol, 1.2 eq) toluenesulfonyl chloride, 0.7 ml (4.08 mmol, 1.2 eq) N-ethyl diisopropylamine and 106 mg (0.17 mmol, 0.05 eq) DMAP-resin, followed by additional 324 mg (1.7 mmol, 0.5 eq) toluenesulfonyl chloride after 3d. The reaction was filtered, 1M HCl was added and the inorganic phase was extracted with CH$_2$Cl$_2$. The combined organic phases were washed with brine, dried over Na$_2$SO$_4$ and were concentrated. The crude product was purified by flash chromatography using ethyl acetate:hexane 1:2 yielding 350 mg (13%) (2S,4R)-4-(4-Methoxy-benzylsulfanyl)-1-(naphthalene-2-sulfonyl)-pyrrolidine-2-carboxylic acid N-methyl-N'N'-bis-(4-methyl-benzenesulfonyl)-hydrazide as white solid, MS: 794 (MH$^+$) and 630 mg (29%) (2S,4R)-4-(4-Methoxy-benzylsulfanyl)-1-(naphthalene-2-sulfonyl)-pyrrolidine-2-carboxylic acid N-methyl-N'-(4-methyl-benzenesulfonyl)-hydrazide as white solid, MS: 640 (MH$^+$).

These compounds were deprotected according to Scheme 2 (step 4) giving:

(2S,4R)-4-Mercapto-1-(naphthalene-2-sulfonyl)-pyrrolidine-2-carboxylic acid N-methyl-N'N'-bis-(4-methyl-benzenesulfonyl)-hydrazide as white crystalline, mp 110° C., MS: 674(MH$^+$).

(2S,4R)-4-Mercapto-1-(naphthalene-2-sulfonyl)-pyrrolidine-2-carboxylic acid N-methyl-N'-(4-methyl-benzenesulfonyl)-hydrazide as white crystalline, mp 103.5° C., MS: 520 (MH$^+$).

(step 25,26) According to procedure (Scheme 4, step 16) was prepared from (2S,4R)-4-(4-Methoxy-benzylsulfanyl)-1-(naphthalene-2-sulfonyl)-pyrrolidine-2-carboxylic acid N-methyl-N'-(4-methyl-benzenesulfonyl)-hydrazide and benzyl bromide (2S,4R)-4-(4-Methoxy-benzylsulfanyl)-1-(naphthalene-2-sulfonyl)-pyrrolidine-2-carboxylic acid N-methyl-N'-benzyl-N'-(4-methyl-benzenesulfonyl)-hydrazide which was directly deprotected according to Scheme 2 (step 4) to give (2S,4R)-4-Mercapto-1-(naphthalene-2-sulfonyl)-pyrrolidine-2-carboxylic acid N-methyl-N'-benzyl-N'-(4-methyl-benzenesulfonyl)-hydrazide as white solid, mp 82.5° C., MS: 610 (MH$^+$).

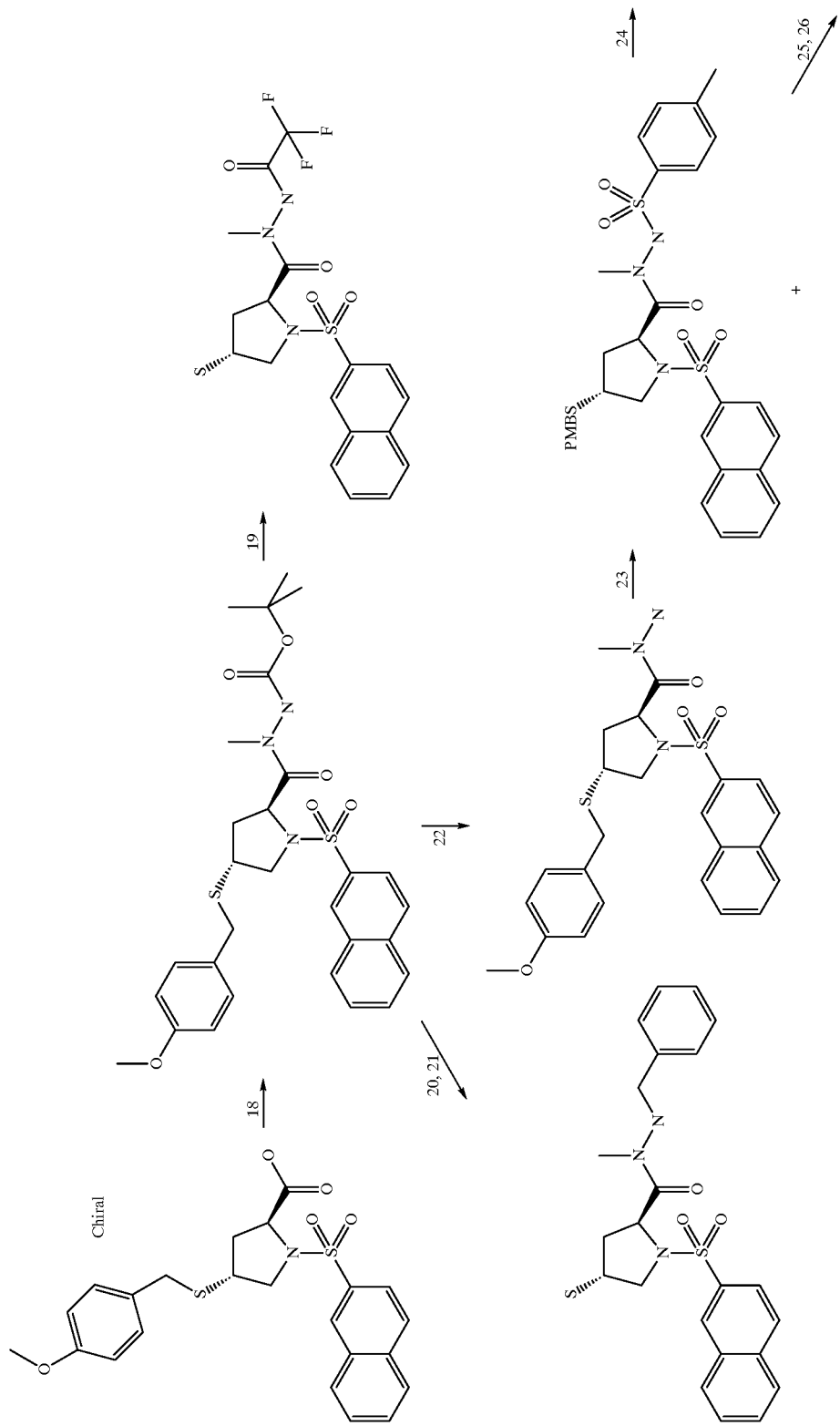

-continued
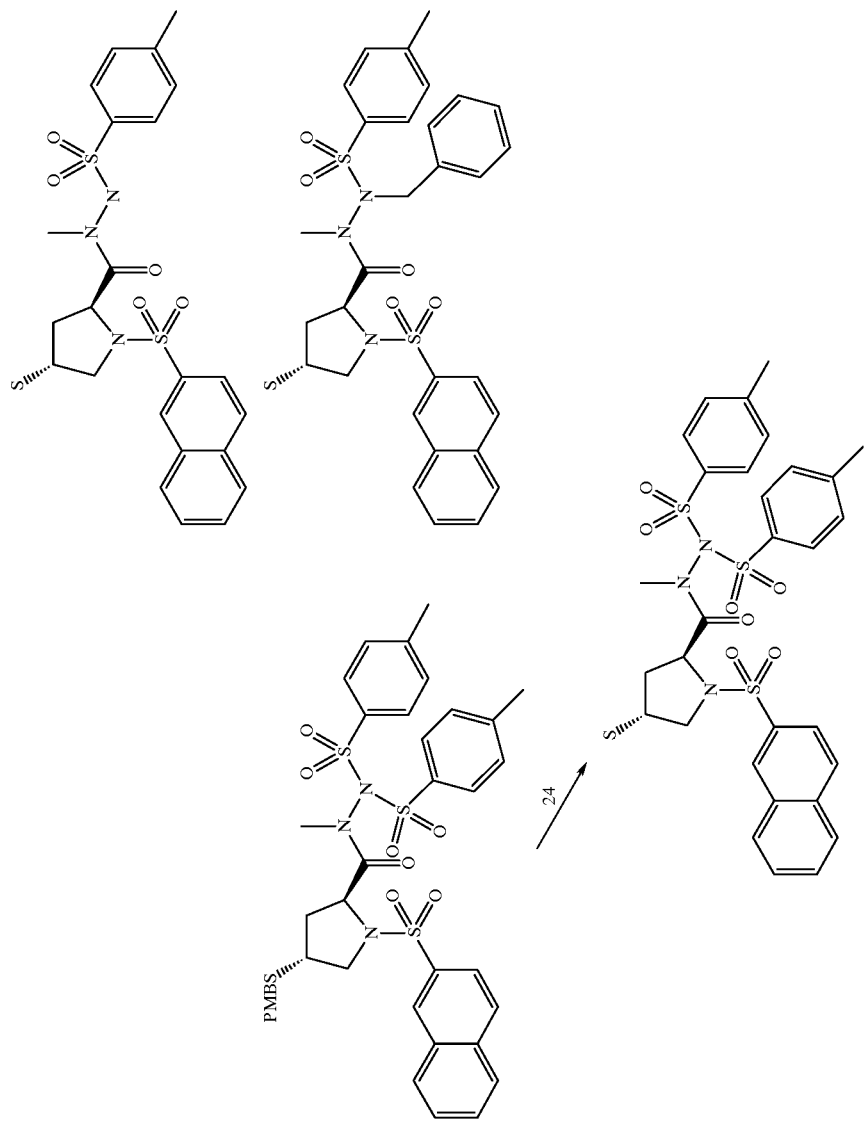
18) N-Hydroxy-2-pyridone, DCC, NEM, CH$_2$Cl$_2$
19) TFA, Et$_3$SiH
20) NaH, BnBr in DMF
21) Et$_3$SiH in TFA
22) TFA, CH$_2$Cl$_2$
23) 1. RSO$_2$Cl, EtiPr$_2$N, DMAP, CH$_2$Cl$_2$, 2. separation
24) Et$_3$SiH in TFA,
25) NaH, BnBr in DMF
26) Et$_3$SiH in TFA

Example 3h

Synthesis of Cyclic Compounds (Scheme 6)

(step 27) To 150 mg (0.25 mmol) (2S,4R)-1-(Naphthalene-2-sulfonyl)-4-tritylsulfanyl-pyrrolidine-2-carboxylic acid hydrazide in 65 ml THF were added 52 µl (0.3 mmol, 1.2 eq) iPr$_2$EtN and 29 µl (0.25 mmol) 4-bromobutyryl chloride at 0° C. The solution was stirred at RT for 2 h, the solution was concentrated and redissolved in ethyl acetate/H$_2$O. The inorganic phase was extracted with ethyl acetate and, the organic phase was washed with brine and dried over Na$_2$SO$_4$. Column chromatography with ethyl acetate:hexane 1:1 yields 170 mg (92%) (2S,4R)-1-(Naphthalene-2-sulfonyl)-4-tritylsulfanyl-pyrrolidine-2-carboxylic acid N'-(4-bromo-butyryl)-hydrazide which was dissolved in 120 ml DMF and treated with 17 mg (0.38 mmol, 55% in mineral oil). NaH and the solution stirred for 2 h, was concentrated and dissolved in ethyl acetate/H$_2$O. The inorganic phase was extracted with ethyl acetate, the organic phase washed with brine and dried over Na$_2$SO$_4$. The crude product was purified by column chromatography yielding 75 mg (45%) (2S,4R)-4-tritylsulfanyl-1-(naphthalene-2-sulfonyl)-pyrrolidine-2-carboxylic acid (2-oxo-pyrrolidin-1-yl)-amide as white foam and 40 mg (25%) (2S,4R)-1-[4-tritylsulfanyl-1-(naphthalene-2-sulfonyl)-pyrrolidine-2-carbonyl]-tetrahydro-pyridazin-3-one as white foam. The two compounds were treated separately in TFA (2 ml/mmol tritylsulfanyl) with 10 eq triethylsilane at 0° C. to RT, until no educt could be detected, to yield (2S,4R)-4-Mercapto-1-(naphthalene-2-sulfonyl)-pyrrolidine-2-carboxylic acid (2-oxo-pyrrolidin-1-yl)-amide as white foam, MS: 420 (MH$^+$) and (2S,4R)-1-[4-Mercapto-1-(naphthalene-2-sulfonyl)-pyrrolidine-2-carbonyl]-tetrahydro-pyridazin-3-one as white foam, MS: 420 (MH$^+$), respectively.

Scheme 6

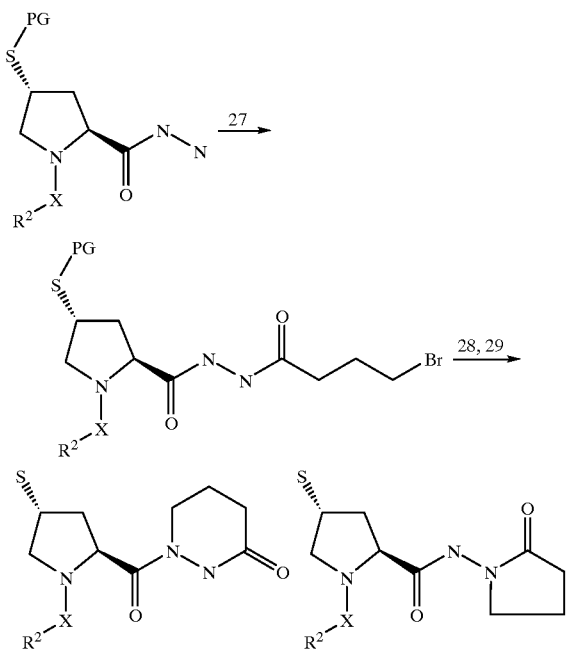

27) Br(CH$_2$)$_3$COCl, iPr$_2$NEt, THF
28) NaH, DMF, RT followed by separation of the two compounds
29) Et$_3$SiH, TFA

Example 4

Solid Phase Synthesis of Hydrazide Derivatives
Building Block Synthesis (Scheme 7)

(2S,4R)-4-(4-Methoxy-benzylsulfanyl)-pyrrolidine-1,2-dicarboxylic acid 1-tert-butyl ester (19.48 g, 53 mmol) was treated with TFA (80 ml) in CH$_2$Cl$_2$ (120 ml) for 15 min. The reaction mixture was concentrated under reduced pressure and the resultant dark red oil was triturated in diethyl ether/n-hexane (1:4 v/v, 860 ml). The precipitated salt was collected and dried under reduced pressure (18.9 g) and directly used in the next step.

The TFA salt (18.9 g, 53 mmol) of (2S, 4R)-4-(4-methoxy-benzylsulfanyl)-pyrrolidine-2-carboxylic acid in 1,4-dioxane/H$_2$O (300 ml) containing NaHCO$_3$ (17.8 g, 212 mmol) was treated with Fmoc-OSu (19.7 g, 58.3 mmol) and magnetically stirred for 16 h. The reaction mixture was diluted with water (400 ml) and washed with diethyl ether (2×). Ethyl acetate (400 ml) and HCl (25%, 50 ml) were added. The organic phase was extracted and washed H$_2$O, NaCl sat. and dried MgSO$_4$. Filtration and concentration under reduced pressure yielded a foam (22.5 g).

Scheme 7

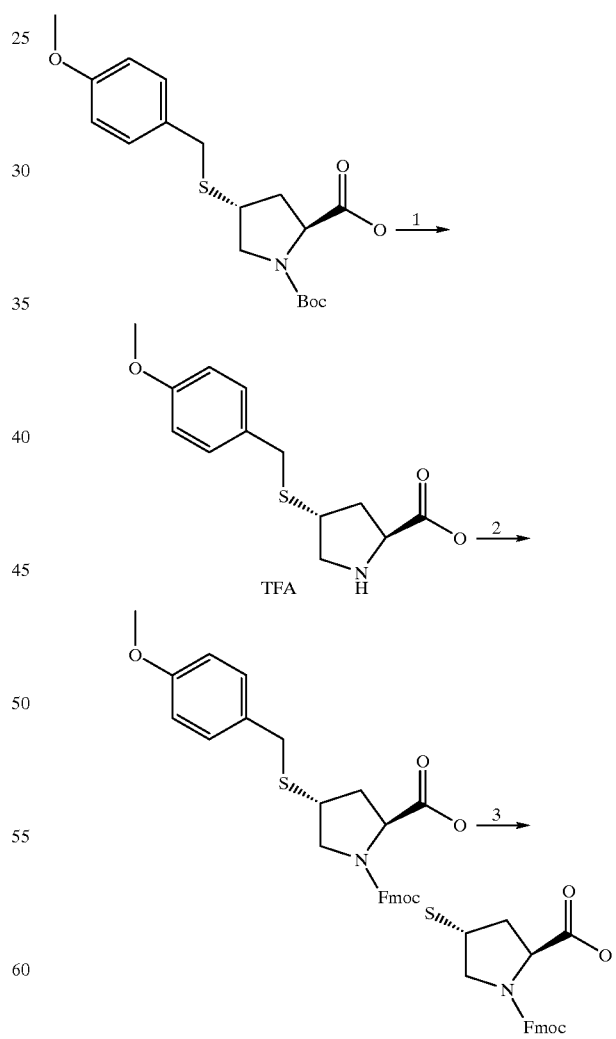

1. 40% TFA/CH$_2$Cl$_2$
2. Fmoc-OSu, NaHCO$_3$, H$_2$O, 1, 4-dioxan
3. TFA, triisopropylsilane The above foam (20.7 g, 42.3 mmol) was dissolved in TFA (350 ml) and triisopropylsilane (43.5 ml) was added. The mixture was refluxed for 0.5 h and concentrated under reduced pressure. Diethyl ether (100 ml) and n-hexanes (300 ml) were added yielding a precipitate. The supernatant was decanted and the precipitate was dried under reduced pressure and high vacuum to yield a white foam (2S, 4R)-4-sulfanyl-1-(fluorenylmethoxycarbonyl)-pyrrolidine-2-carboxylic acid (9.6 g, MS: 370 MH$^+$)

Resin Derivatization (Scheme 8)

The linker 4-(α,α-diphenylhydroxymethyl)benzoic acid (18.3 g, 60 mmol) was activated using TPTU (17.8 g, 60 mmol), DIEA (30.8 ml, 180 mmol) in DMF(abs., 250 ml) for 3 min. The mixture was added to a flask containing benzhydrylamine resin (loading-NH$_2$ 0.9 mmol/g, 44.4 g) and the flask was shaken for 1 h. The resin was collected on a filter and washed (3×alternating DMF/isopropanol), CH$_2$Cl$_2$, ether and dried: 54.65 g, 0.65 mmol/g (loading based on mass increase).

To the CH$_2$Cl$_2$ washed resin above (46.9 g, 30 mmol), was added a mixture of (2S, 4R)-4-sulfanyl-1-(naphthalene-2-sulfonyl)-pyrrolidine-2-carboxylic acid (12.2 g, 36 mmol) in CH$_2$Cl$_2$ (abs. 550 ml), TFA (80 ml). The red colored mixture was shaken for 1.5 h and the resin was then filtered, washed (3×alternating CH$_2$Cl$_2$/isopropanol), CH$_2$Cl$_2$, ether and dried: 42 g, 0.65 mmol/g (loading based on mass increase).

To the CH$_2$Cl$_2$ washed resin above (33.5 g, 22 mmol), was added a mixture of (2S, 4R)-4-sulfanyl-1-(fluorenylmethoxycarbonyl)-pyrrolidine-2-carboxylic acid (9.7 g, 26 mmol) in CH$_2$Cl$_2$ (abs. 450 ml), TFA (67 ml). The red colored mixture was shaken for 1.5 h and the resin was then filtered, washed (3×alternating CH$_2$Cl$_2$/isopropanol), CH$_2$Cl$_2$, ether and dried: 42 g, 0.59 mmol/g (loading based on mass increase).

Scheme 8

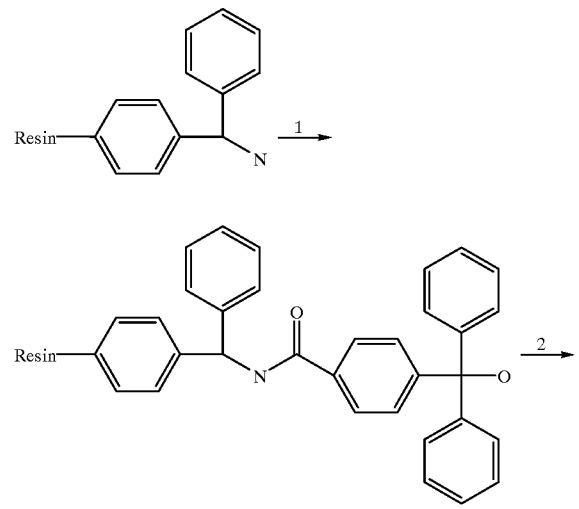

-continued

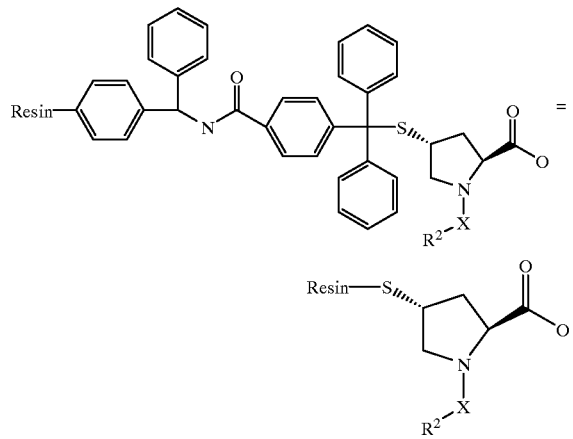

1. 4-(α, α-diphenylhydroxymethyl)benzoic acid, O-(1, 2-dihydro-2-oxopyrid-1-yl)-N, N, N', N'-tetramethyluronium tertrafluoroborate (TPTU), Huenig's Base
2. (2S, 4R)-4-sulfanyl-1-(naphthalene-2-sulfonyl)-pyrrolidine-2-carboxylic acid or (2S, 4R)-4-sulfanyl-1-(fluorenylmethoxycarbonyl)-pyrrolidine-2-carboxylic acid, TFA, CH$_2$Cl$_2$ Example 5

Parallel Chemistry on Solid Phase (Scheme 9)

Typical Procedure: Steps 1,2

Resin derivatized with (2S, 4R)-4-sulfanyl-1-(naphthalene-2-sulfonyl)-pyrrolidine-2-carboxylic acid (0.4 g, 0.26 mmol) above, was treated with DMF (abs. 5 ml), TPTU (0.18 g, 0.61 mmol), DIEA (0.21 ml, 1.21 mmol) for 10 min. The DMF solution was removed under vacuum and the reaction flask was charged with benzyloxycarbonyl hydrazide (0.13 g, 0.77 mmol) in DMF (abs. 3 ml). The reaction mixture was shaken for 0.5 h and the resin was collected at the filter, washed (3×alternating DMF/isopropanol), CH$_2$Cl$_2$, ether and dried.

The resin (440 mg) was treated with 40% TFA/CH$_2$Cl$_2$ (10 ml), triisopropylsilane (0.5 ml) for 10 min and the filtrate was collected and concentrated under reduced pressure and the residue was freeze-dried from acetic acid (10 ml) yielding 41 mg (2S, 4R)-N'-[4-mercapto-1-(naphthalene-2-sulfonyl)-pyrrolidine-2-carbonyl]-hydrazinecarboxylic acid benzyl ester as a white lyophilisate, MS: 508.3 (MNa$^+$).

Other compounds prepared in parallel, via the above procedure, were indicated in Table 1.

Scheme 9

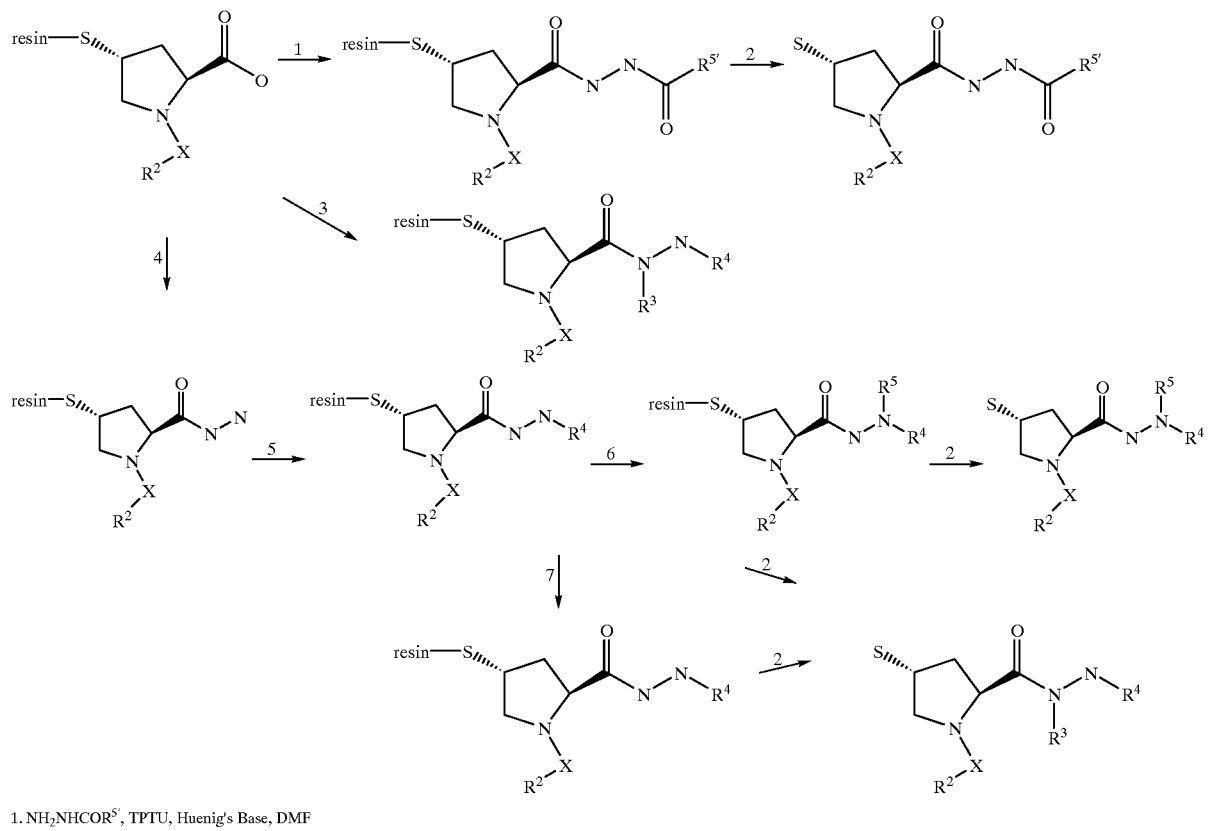

1. NH₂NHCOR⁵', TPTU, Huenig's Base, DMF
2. TFA/CH₂Cl₂, triisopropylsilane
3. NH₂NHR4, TPTU, Huenig's Base, DMF
4. NH₂NH₂. H₂O, TPTU, DMF
5. R4SO₂Cl, DMF gives two products (R3 = R4) which are separated after detachment from the resin
6. R⁵-halogenide, DBU, DMF
7. 20% piperidine/DMF then R²-X-halogenide, pyridine in DMF Typical Procedure: Steps 3,2

Resin derivatized with (2S, 4R)-4-sulfanyl-1-(naphthalene-2-sulfonyl)-pyrrolidine-2-carboxylic acid (0.5 g, 0.33 mmol) above, was treated with DMF (abs. 5 ml), TPTU (0.19 g, 0.65 mmol), DIEA (0.22 ml, 1.3 mmol) for 10 min. The DMF solution was removed under vacuum and the reaction flask was charged with 4-methoxybenzenesulfonyl hydrazide (0.20 g, 1.00 mmol) in DMF (abs. 5 ml). The reaction mixture was shaken for 1 h and the resin was collected at the filter, washed (3×alternating DMF/isopropanol), CH₂Cl₂, ether and dried.

The resin (540 mg) was treated with 40% TFA/CH₂Cl₂, triisopropylsilane (0.5 ml) for 15 min and the filtrate was collected and concentrated under reduced pressure and the residue was purified by prep.RP-HPLC and the desired fractions were pooled and freeze-dried from acetic acid (10 ml) yielding (2S, 4R)-4-mercapto-1-(naphthalene-2-sulfonyl)-pyrrolidine-2-carboxylic acid N'-(4-methoxy-benzenesulfonyl)-hydrazide as a white lyophilisate, MS: 520.1 (MH³¹)

Other compounds prepared in parallel, via the above procedure, were indicated in Table 1.

Typical Procedure: Steps 3,6,2

Resin derivatized with (2S, 4R)-4-sulfanyl-1-(naphthalene-2-sulfonyl)-pyrrolidine-2-carboxylic acid (4.3 g, 2.75 mmol) above, was treated with DMF (abs. 30 ml), TPTU (1.63 g, 5.50 mmol), DIEA (1.41 ml, 8.25 mmol) for 15 min. The DMF solution was removed under vacuum and the reaction flask was charged with toluene-4-sulfonhydrazide (1.54 g, 8.25 mmol) in DMF (abs. 30 ml). The reaction mixture was shaken for 16 h and the resin was collected at the filter, washed (3×alternating DMF/isopropanol), CH₂Cl₂, ether and dried.

A Typical Alkylation Step e.g.,

To the resin (0.8 g, 0.45 mmol) was added DMF (abs. 10 ml), diazabicyclo[5.4.0]undec-7-ene (0.08 ml, 0.54 mmol), 2,5-difluorobenzylbromide (0.11 g, 0.54 mmol) and the mixture shaken for 16 h and the resin was collected at the filter, washed (3×alternating DMF/isopropanol), CH₂Cl₂, ether and dried.

The resin (0.16 g) was treated with 40% TFA/CH₂Cl₂ (10 ml), triisopropylsilane (0.5 ml) for 15 min and the filtrate was collected and concentrated under reduced pressure and the residue was purified by prep.RP-HPLC and the desired fractions were pooled and freeze-dried from acetic acid yielding (2S, 4R)-4-mercapto-1-(naphthalene-2-sulfonyl)-pyrrolidine-2-carboxylic acid N'-(2,5-difluorobenzyl)-N'-(4-methyl-benzenesulfonyl)-hydrazide as a white lyophilisate, MS: 632.0 (MH⁺).

Other compounds prepared in parallel, via the above procedure, were indicated in Table 1. Disubstituted products were also obtained.

Typical Procedure: Steps 4,5,2

Resin derivatized with (2S, 4R)-4-sulfanyl-1-(naphthalene-2-sulfonyl)-pyrrolidine-2-carboxylic acid (1.0 g, 0.65 mmol) above, was treated with DMF (abs. 10 ml), TPTU (0.39 g, 1.3 mmol), DIEA (0.45 ml, 2.6 mmol) for 10 min. The DMF solution was removed under vacuum and the reaction flask was charged with hydrazine hydrate (25%, 0.42 ml, 3.25 mmol) in DMF (abs. 8 ml). The reaction mixture was shaken for 1 h and the resin was collected at the filter, washed (3×alternating DMF/isopropanol), $CH_2Cl_2$, ether and dried.

To this resin (0.22 g, 0.14 mmol) was added DMF (abs. 3 ml), DIEA (0.10 ml, 0.60 mmol), 4-fluorobenzenesulfonyl chloride (0.11 g, 0.56 mmol) and the mixture shaken for 3.5 h and the resin was collected at the filter, washed (3×alternating DMF/isopropanol), $CH_2Cl_2$, ether and dried.

The resin (0.25 mg) was treated with 40% TFA/$CH_2Cl_2$ (10 ml), triisopropylsilane (0.5 ml) for 15 min and the filtrate was collected and concentrated under reduced pressure and the residue was purified by prep.RP-HPLC and the desired fractions were pooled and freeze-dried from acetic acid (10 ml) yielding (2S, 4R)-4-mercapto-1-(naphthalene-2-sulfonyl)-pyrrolidine-2-carboxylic acid N'-(4-fluoro-benzenesulfonyl)-hydrazide as a white lyophilisate, MS: 510.2 (MH$^-$).

Other compounds prepared in parallel, via the above procedure, were indicated in Table 1.

Typical Procedure: Steps 3,7,2

Resin derivatized with ((2S, 4R)-4-sulfanyl-1-(fluorenylmethoxycarbonyl)-pyrrolidine-2-carboxylic acid (20.1 g, 11.9 mmol) above, was treated with DMF (abs. 150 ml), TPTU (7.1 g, 23.8 mmol), DIEA (6.1 ml, 35.7 mmol) for 10 min. The DMF solution was removed under vacuum and the reaction flask was charged with toluene-4-sulfon hydrazide (6.65 g, 35.7 mmol) in DMF (abs. 100 ml). The reaction mixture was shaken for 16 h and the resin was collected at the filter, washed (3×alternating DMF/isopropanol), DMF.

Fmoc group removal was achieved with 20% piperidine/DMF (2×5 min).

Pyrrolidine substitution reactions followed e.g.,

To this resin (0.60 g, 0.30 mmol) was added DMF (abs. 6 ml), pyridine (0.12 ml, 1.50 mmol), 8-quinolinesulfonyl chloride (0.08 g, 0.36 mmol) and the mixture shaken for 16 h and the resin was collected at the filter, washed (3×alternating DMF/isopropanol), $CH_2Cl_2$, ether and dried.

The resin (0.25 mg) was treated with 40% TFA/$CH_2Cl_2$ (10 ml), triisopropylsilane (0.5 ml) for 15 min and the filtrate was collected and concentrated under reduced pressure and the residue was purified by prep.RP-HPLC and the desired fractions were pooled and freeze-dried from acetic acid (10 ml) yielding (2S, 4R)-4-mercapto-1-(naphthalene-2-sulfonyl)-pyrrolidine-2-carboxylic acid N'-(4-fluoro-benzenesulfonyl)-hydrazide as a white lyophilisate, MS: 505.3(MH$^-$)

Other compounds prepared in parallel, via the above procedure, were indicated in

TABLE 1

| Name | Ion Spray MS | Educt | Steps: Scheme 9 |
|---|---|---|---|
| (2S,4R)-4-Mercapto-1-(naphthalene-2-sulfonyl)-pyrrolidine-2-carboxylic acid N'-phenyl-hydrazide | M+H 428.4 | phenylhydrazide | 3,2 |
| Benzoic acid (2S,4R)-N'-[4-mercapto-1-(naphthalene-2-sulfonyl)-pyrrolidine-2-carbonyl]-hyrazide | M+H 456.3 | Benzoic acid hydrazide | 1,2 |
| (2S,4R)-N'-[4-Mercapto-1-(naphthalene-2-sulfonyl)-pyrrolidine-2-carboxyl]-hydrazinecarboxylic acid methyl ester | M+H 410.3 | carboxylic acid methylester hydrazide | 1,2 |
| (2S,4R)-N'-[4-Mercapto-1-(naphthalene-2-sulfonyl)-pyrrolidine-2-carbonyl]-hydrazinecarboxylic acid benzyl ester | M+Na 508.3 | benzyloxycarbonyl hydrazide | 1,2 |
| Furan-2-carboxylic acid (2S,4R)-N'-[4-mercapto-1-(naphthalene-2-sulfonyl)-pyrrolidine-2-carboxynyl]-hydrazide | M+H 446.3 | 2-furoic acid hyrazide | 1,2 |
| Nicotinic acid (2S,4R)-N'-[4-mercapto-1-(naphthalene-2-sulfonyl)-pyrrolidene-2-carbonyl]-hyadrazide trifluoro-acetate (1:1) | M+H 457.3 | Nicotinic acid hydrazide | 1,2 |
| (2S,4R)-4-Mercapto-1-(naphthalene-2-sulfonyl)-pyrrolidine-2-carboxylic acid N'-(4-methyl-benzenesulfonyl)-hydrazide | M+NH4 523.2 | toluene-4-sulfon hydrazide | 3,2 |
| (2S,4R)-4-Mercapto-1-(naphthalene-2-sulfonyl)-pyrrolidine-2-carboxylic acid hydrazide trifluoro-acetate (1:1) | M+H 352.2 | hydrazide hydrate | 4,2 |
| (2S,4R)-4-Mercapto-1-(naphthalene-2-sulfonyl)-pyrrolidine-2-carboxylic acid N'-(4-methoxy-benzenesulfonyl)-hydrazide | M−H 520.1 | 4-methoxybenzenesulfonyl hydrazide | 3,2 |
| (2S,4R)-4-Mercapto-1-(naphthalene-2-sulfonyl)-pyrrolidine-2-carboxylic acid N'-(4-methyl-benzolyl)-hydrazide | M+H 470.2 | 4-methyl-benzoyl-hydrazide | 1,2 |
| (2S,4R)-4-Mercapto-1-(naphthalene-2-sulfonyl)-pyrrolidine-2-carboxylic acid N'-(thiophen-3-yl-acetyl)-hydrazide | M+H 476.1 | thiophen-3-yl-acetyl-hydrazide | 1,2 |
| (2S,4R)-4-Mercapto-1-naphthalene-2-sulfonyl)-pyrrolidine-2-carboxylic acid N'-(1H-indol-3-yl-acetyl)-hydrazide | M+H 509.3 | 1H-indo;-3-yl-acetyl-hydrazide | 1,2 |
| (2S,4R)-4-Mercapto-1-(naphthalene-2-sulfonyl)-pyrrolidine-2-carboxylic acid N'-(thiophene-2-carbonyl)-hydrazide | M+H 462.2 | thiophene-2-carbonyl-hydrazide | 1,2 |

TABLE 1-continued

| Name | Ion Spray MS | Educt | Steps: Scheme 9 |
|---|---|---|---|
| (2S,4R)-N'-[4-Mercapto-1-(naphthalene-2-sulfonyl)-pyrrolidine-2-carbonyl]-hydrazinecarboxylic acid (3-fluoro-phenyl)-amide | M+H 489.2 | 3-fluoro-phenylamide hydrazide | 1,2 |
| (2S,4R)-4-Mercapto-1-(naphthalene-2-sulfonyl)-pyrrolidine-2-carboxylic acid N'-benzenesulfonyl-hydrazide | M+H 490.2 | benzenesulfonyl hydrazide | 3,2 |
| (2S,4R)-4-Mercapto-1-(naphthalene-2-sulfonyl)-pyrrolidine-2-carboxylic acid N'-acetyl-hydrazide | M+H 394.3 | acetyl hydrazide | 1,2 |
| Isonicotinic acid (2S,4R)-N'-[4-mercapto-1-(naphthalene-2-sulfonyl)-pyrrolidine-2-carbonyl]-hydrazide trifluoro-acetate (1:1) | M+H 547.3 | Isonicotinic acid hydrazide | 1,2 |
| (2S,4R)-N'-[4-Mercapto-1-(naphthalene-2-sulfonyl)-pyrrolidine-2-carbonyl]-hydrazinecarboxylic acid phenylamide | M+H 471.2 | phenylamide carboxylic acid | 1,2 |
| (2S,4R)-4-Mercapto-1-(naphthalene-2-sulfonyl)-pyrrolidine-2-carboxylic acid N'-dimethylaminoacetyl-hydrazide trifluoro-acetate (1:1) | M+H 437.3 | dimethylaminoacetyl hydrazide | 1,2 |
| (2S,4R)-4-Mercapto-1-(naphthalene-2-sulfonyl)-pyrrolidine-2-carboxylic acid N',N'-bis-(4-methyl-benzenesulfonyl)-hydrazide | M+NH4 677.3 | toluene-4-sulfon hydrazide | 3,2 |
| (2S,4R)-4-Mercapto-1-(naphthalene-2-sulfonyl)-pyrrolidine-2-carboxylic acid N-methyl-N'(4-methyl-benzenesulfonyl)-hydrazide | M+NH4 537.2 | 1. toluene-4-sulfon hydrazide 2. iodomethane | 3,6,2 |
| (2S,4R)-4-Mercapto-1-(naphthalene-2-sulfonyl)-pyrrolidine-2-carboxylic acid N,N'-dimethyl-N'-( methyl-benzenesulfonyl)-hydrazide | M+H 534.2 | 1. toluene-4-sulfon hydrazide; 2.iodomethane | 3,6,2 |
| (2S,4R)-4-Mercapto-1-(naptahlene-2-sulfonyl)-pyrrolidine-2-carboxylic acid N'-(2,4-difluoro-benzenesulfonyl)-hydrazide | M+NH4 545.1 | 2,4-difluorosulfonyl chloride | 4,5,2 |
| (2S,4R)-4-Mercapto-1-(naphthalene-2-sulfonyl)-pyrrolidine-2-carboxylic acid N'-(2-fluoro-benzenesulfonyl)-hydrazide | M+H 510.2 | 2-fluoro-benzenesulfonyl chloride | 4,5,2 |
| (2S,4R)-4 Mercapto-1-(naptahlene-2-sulfonyl)-pyrrolidine-2-carboxylic acid N'(4-fluro-benzenesulfonyl)-hydrazide | M+H 510.2 | 4-fluoro-benzenesulfonyl chloride | 4,5,2 |
| (2S,4R)-4-Mercapto-1-(naphthalene-2-sulfonyl)-pyrrolidine-2-carboxylic acid N,N'-bis-(4-fluro-benzenesulfonyl)-hydrazide | M+NH4 685.2 | 4-fluoro-benzenesulfonyl choride | 4,5,2 |
| (2S,4R)-4-Mercapto-1- (naphthalene-2-sulfonyl)-pyrrolidine-2-carboxylic acid N'-methanosulfonyl-hydrazide | M+NH4 447.2 | methanesulfonyl chloride | 4,5,2 |
| (2S,4R)-4-Mercapto-1-(naphthalene-2-sulfonyl)-pyrrolidine-2-carboxylic acid N'-thiopene-2-sulfonyl-hydrazide | M+H 498.0 | 2-thiophenesulfonyl chloride | 4,5,2 |
| (2S,4R)-N-[4-[N''-[4-Mercapto-1-(naphthalene-2-sulfonyl)-pyrrolidine-2-carbonyl]-hydrazinosulfonyl]-phenyl]-acetamide | M+NH4 566.1 | N-acetylsulfanilyl chloride | 4,5,2 |
| (2S,4R)-N'-[4-Mercapto-1-(naphthalene-2-sulfonyl)-pyrrolidine-2-carbonyl]-hydrazinecarboxylic acid dimethylamide | M+H 459.3 | N,N-dimethylsulfamoyl chloride | 4,5,2 |
| (2S,4R)-4-Mercapto-1-(napthalene-2-sulfonyl)-pyrrolidine-2-carboxylic acid N'(4-methylsulfonyl-benzenesulfonyl)-hydrazide | M+NH4 569.7 | 4-methylsulfonylbenzenesulfonyl chloride | 4,5,2 |
| (2S,4R)-Mercapto-1-(naphthalene-2-sulfonyl)-pyrrolidine-2-carboxylic acid N'-(3,5-dimethyl-isoxazole-4-sulfonyl)-hydrazide | M+H 511.2 | 3,5-dimethylisoxazole-4-sulfonyl chloride | 4,5,2 |
| (2S,4R)-Mercapto-(naphthalene-2-sulfonyl)-pyrrolidine-2-carboxylic acid N,N'-bis-(3,5-dimethyl-isoxazole-4-sulfonyl)-hydrazide | M+H 670.1 | 3,5-dimethylisoxazole-4-sulfonyl chloride | 4,5,2 |
| (2S,4R)-Mercapto-1-(naphthalene-2-sulfonyl)-pyrrolidine-2-carboxylic acid N'-isopropanesulfonyl-hydrazide | M+NH4 475.2 | isoproplsulfonyl chloride | 4,5,2 |
| (2S,4R)-4-Mercapto-1-1(naphthlene-2-sulfonyl)-pyrrolidine-2-carboxylic acid N'-(3-fluoro-benzenesulfonyl)-hydrazide | M+H 510.3 | 3-fluro-benzenesulfonyl chloride | 4,5,2 |
| (2S,4R)-4-Mercapto-1-(naphthalene-2-sulfonyl)-pyrrolidine-2-carboxylic acid N'N'-bis-(3-fluoro-benzenesulfonyl) hydrazide | M+NH4 684.9 | 3-fluoro-benzenesulfonyl chloride | 4,5,2 |
| (2S,4R)-4-Mercapto-1-(napthalene-2-sulfonyl)-pyrrolidine-2-carboxylic acid N'-cyclopropylmethyl-N'-(4-methyl- | M+H 558.1 | 1. Toluene-4-sulfon hydrazide 2. Bromomethyl | 3,6,2 |

TABLE 1-continued

| Name | Ion Spray MS | Educt | Steps: Scheme 9 |
|---|---|---|---|
| benzenesulfonyl)-hydrazide (2S,4R)-4-Mercapto-1-(naphthalene-2-sulfonyl)-pyrrolidine-carboxylic acid N'(2,5-difluoro-benzyl)-hydrazide | M+H 478.2 | cyclopropane alpha-bromo-2,5-difluorotoluene | 4,5,2 |
| (2S,4R)-4-Mercapto-1-(naphthalene-2-sulfonyl)-pyrrolidine-2-carboxylic acid N'-(4-methy-benzenesulfonyl)-N'-(2,4,5-trifluoro-benzyl)-hydrazide | M+NH4 667.1 | 1. Toluene-4-sulfon hydrazide 2. 2,4,5-trifluorobenzyl bromide | 3,6,2 |
| (2S,4R)-4-Mercapto-1-(naphthalene-2-sulfonyl)-pyrrolidine-2-carboxylic acid N'-(2,5-difluoro-benzyl)-N'-(4-methyl-benzesulfonyl)-hydrazide | M+H 632.0 | 1. Toluene-4-sulfon chloride 2. 2,5-trifluorobenzyl bromide | 3,6,2 |
| (2S,4R)-4-Mercapto-1-(naphthalene-2-sulfonyl)-pyrrolidine-2-carboxylic acid N'-isopropyl-N'-(4-methyl-benzensulfonyl)-hydrazide | M+H 548.1 | 1. Toluene-4-sulfon hydrazide 2. Isopropyl iodide | 3,6,2 |
| (2S,4R)-N'-[4-Mercapto-1-(naphthalene-2-sulfonyl)-pyrrolidine-2-carbnyl]-N-(4-methyl-benzenesulfonyl)-hydrazino]-acetic acid | M+H 564.1 | 1. Toluene-4-sulfon hydrazide 2. Tert.-butyl bromoacetate | 3,6,2 |
| (2S,4R)-4-Mercapto-2-[N'-(4-(methyl-benzenesulfonyl)-hydrazinocarbonyl]-pyrrolidine-1-carboxylic acid benzyl ester | M−H 448.2 | 1. Toluene-4-sulfon hydrazide 2. Benzyloxycarbonyl chloride | 3,7,2 |
| (2S,4R)-1-(2,6-Difluoro-benzoyl)-4-mercapto-pyrrolidine-2-carboxylic acid N'-(4-methyl benzenesulfonyl)-hydrazide | M−H 454.3 | 1. Toluene-4-sulfon hydrazide 2. 2,6-Difluoro-benzoyl chloride | 3,7,2 |
| (2S,4R)-4-Mercapto-1-(quinoline-8-sulfonyl)-pyrrolidine-2-carboxylic acid N'-(4-metyhl-benzenesulfonyl)-hydrazide | M−H 505.3 | 1. Toluene-4-sulfon hydrazide 2. 8-quinolinesulfonyl chloride | 3,7,2 |
| (2S,4R)-4-Mercapto-2-[N'-(4-methyl-benzenesulfonoyl)-hydrazinocarbonyl]-pyrrolidine-1-carboxylic acid butyl ester | M−H 414.3 | 1. Toluene-4-sulfon hydrazide 2. Butyl chloroformate | 3,7,2 |
| (2S,4R)-4-Mercapto-2-[N'-(4-methyl-benzenesulfonyl)-hydrazinocarbonyl]-pyrrolidine-1-sulfonic acid amide | M−H 393.0 | 1. Toluene-4-sulfon hydrazide 2. Chloro-sulfonic acid amide | 3,7,2 |
| (2S,4R)-1-(Biphenyl-4-sulfonyl)-4-mercapto-pyrrolidine-2-carboxylic acid N'-(4-methyl-benzenesulfonyl)-hydrazide | M+NH4 549.4 | 1. Toluene-4-sulfon hydrazide 2. Biphenyl-4-sulfonyl chloride | 3,7,2 |
| (2S,4R)-1-(3-Fluoro-benzenesulfonyl)-4-mercapto-pyrrolidine-2-carboxylic acid N'-(4-methyl-benzenesulfonyl)-hydrazide | M+NH4 491.4 | 1. Toluene-4-sulfon hydrazide 2. 3-Fluoro-benzenesulfonyl chloride | 3,7,2 |
| (2S,4R)-1-(2-Fluoro-benzenesulfonyl)-4-mercapto-pyrrolidine-2-carboxylic acid N'-(4-methyl-benzenesulfonyl)-hydrazide | M+NH4 491.4 | 1. Toluene-4-sulfon hydrazide 2. 2-Fluoro-benzenesulfonyl chloride | 3,7,2 |
| (2S,4R)-4-Mercapto-1-(2,4,5-trifluoro-benzenesulfonyl)-pyrrolidine-2-carboxylic acid N'-(4-methyl-benzenesulfonyl)-hydrazide | M+NH4 527.3 | 1. Toluene-4-sulfon hydrazide 2. 2,4,5-Fluoro-benzenesulfonyl chloride | 3,7,2 |
| (2S,4R)-4-Mercapto-1-(4-phenoxy-benzenesulfonyl)-pyrrolidine-2-carboxylic acid N'-4(methyl-benzenesulfonyl)-hydrazide | M+NH4 565.4 | 1. Toluene-4-sulfon hydrazide 2. 4-phenoxy-benzenesulphonyl chloride | 3,7,2 |
| (2S,4R)-1-(Biphenyl-4-sulfonyl)-4-mercapto pyrrolidine-2-carboxylic acid N'-methyl-N'-(4-methyl-benzenesulfonyl)-hydrazide | M+H 546.4 | 1. Toluene-4-sulfon hydrazide 2. Biphenyl-4-sulfonyl chloride 3. iodomethane | 3,7,6,2 |
| (2S,4R)-1-(3-Fluoro-benzenesulfonyl)-4-mercapto-pyrrolidine-2-carboxylic acid N'-methyl-N'-(4-methyl-benzenesulfonyl)-hydrazide | M+H 488.4 | 1. Toluene-4-sulfon hydrazide 2. 3-Fluoro-benzenesulfonyl chloride 3. iodomethane | 3,7,6,2 |
| (2S,4R)-1-(2-Fluoro-benzenesulfonyl)-4-mercapto-pyrrolidine-2-carboxylic acid N'-methyl-N'-(4-methyl-benzenesulfonyl)-hydrazide | M+H 488 | 1. Toluene-4-sulfon hydrazide 2. 2-Fluoro-benzenesulfonyl chloride 3. iodomethane | 3,7,6,2 |
| (2S,4R)-4-Mercapto-1-(2,4,5-trifluoro-benzenesulfonyl)-pyrrolidine-2-carboxylic acid N'-methyl-N'-(4-methyl-benzenesulfonyl)- | M+NH4 541.3 | 1. Toluene-4-sulfon hydrazide 2. 2-Fluoro- | 3,7,6,2 |

TABLE 1-continued

| Name | Ion Spray MS | Educt | Steps: Scheme 9 |
|---|---|---|---|
| hydrazide | | benzenesulfonyl chloride<br>3. iodomethane | |
| (2S,4R)-4-Mercapto-1-(4-phenoxy-benzenesulfonyl)-pyrrolidine-2-carboxylic acid N'-methyl-N'-(4-methyl-benzenesulfonyl)-hydrazide | M+H 562 | 1. Toluene-4-sulfon hydrazide<br>2. 4-phenoxy-benzenesulfonyl chloride<br>3. iodomethane | 3,7,6,2 |
| (2S,4R)-4-Mercapto-1-(4-propyl-benzenesulfonyl)-pyrrolidine-2-carboxylic acid N'-(4-methyl-benzenesulfonyl)-hydrazide | M−H 496.1 | 1. Toluene-4-sulfon hydrazide<br>2. 4-propyl-benzenesulfonyl chloride | 3,7,2 |
| (2S,4R)-1-(3,5-Dimethyl-isoxazole-4-sulfonyl)-4-mercapto-pyrrolidine-2-carboxylic acid N'-(4-methyl-benzenesulfonyl)-hydrazide | M−H 473.0 | 1. Toluene-4-sulfon hydrazide<br>2. 3,5-Dimethyl-isoxazole-4-sulfonyl chloride | 3,7,2 |
| (2S,4R)-4-Mercapto-1-(4-methanesulfonyl-benzenesulfonyl)-pyrrolidine-2-carboxylic acid N'-(4-methyl-benzenesulfonyl)-hydrazide | M−H 532.0 | 1. Toluene-4-sulfon hydrazide<br>2. 4-methanesulfonyl-benzenesulfonyl chloride | 3,7,2 |
| (2S,4R)-4-Mercapto-1-thiophene-2-sulfonyl-pyrrolidine-2-carboxylic acid N'-(4-methyl-benzenesulfonyl)-hydrazide | M−H 460.2 | 1. Toluene-4-sulfon hydrazide<br>2. thiophene-2-sulfonyl chloride | 3,7,2 |
| (2S,4R)-4-Mercapto-2-[N'-(4-methyl-benzenesulfonyl)-hydrazinocarbonyl]-pyrrolidine-1-sulfonic acid dimethylamide | M−H 421.3 | 1. Toluene-4-sulfon hydrazide<br>2. Chloro sulfonic acid dimethylamide | 3,7,2 |
| (2S,4R)-1-(4-Fluoro-benzenesulfonyl)-4-mercapto-pyrrolidine-2-carboxylic acid N'-(4-methyl-benzenesulfonyl)-hydrazide | M−H- 472.1 | 1. Toluene-4-sulfon hydrazide<br>2. 4-Fluoro-benzenesulfonyl chloride | 3,7,2 |
| (2S,4R)-1-Isopropanesulfonyl-4-mercapto-pyrrolidine-2-carboxylic acid N'-(4-methyl-benzenesulfonyl)-hydrazide | M−H 420.3 | 1. Toluene-4-sulfon hydrazide<br>2. Isopropanesulfonyl chloride | 3,7,2 |
| (2S,4R)-1-(2,4-Difluoro-benzenesulfonyl)-4-mercapto-pyrrolidine-2-carboxylic acid N'-(4-methyl-benzenesulfonyl)-hydrazide | M−H 490.2 | 1. Toluene-4-sulfon hydrazide<br>2. 2,4-Difluoro-bezenesulfonyl chloride | 3,7,2 |
| (2S,4R)-4-Mercapto-1-(2,3,4,5,6-pentafluoro-benzenesulfonyl)-pyrrolidine-2-carboxylic acid N'-(-methyl-benzenesulfonyl)-hydrazide | M−H 544.0 | 1. Toluene-4-sulfon hydrazide<br>2. 2,3,4,5,6-pentafluoro-benzenesulfonyl chloride | 3,7,2 |
| (2S,4R)-4-Mercapto-1-methanesulfonyl-pyrrolidine-2-carboxylic acid N'-(4-methyl-benzenesulfonyl)-hydrazide | M−H 392.1 | 1. Toluene-4-sulfon hydrazide<br>2. methanesulfonyl chloride | 3,7,2 |
| (2S,4R)-1-(2,5-Difluoro-benzenesulfonyl)-4-mercapto-pyrrolidine-2-carboxylic acid N'-(4-methyl-benzenesulfonyl)-hydrazide | M−H 490.2 | 1. Toluene-4-sulfon hydrazide<br>2. 2,5-Difluoro-benzenesulfonyl chloride | 3,7,2 |
| (2S,4R)-4-Mercapto-1-(4-methyl-benzenesulfonyl)-pyrrolidine-2-carboxylic acid N'-(-methyl-benzenesulfonyl)-hydrazide | M−H 468.1 | 1. Toluene-4-sulfon hydrazide<br>2. 4-methyl-benzenesulfonyl chloride | 3,7,2 |
| (2S,4R)-N-[4-[4[Mercapto-2-[N'-(4-methyl-benzenesulfonyl)-hydrazinocarbonyl]-pyrrolidine-1-sulfonyl]-phenyl)-acetamide | M−H 511.2 | 1. Toluene-4-sulfon hydrazide<br>2. 4-acetamide phenylsulfonyl chloride | 3,7,2 |
| (2S,4R)-1-(4-Butoxy-benzenesulfonyl)-4-mercapto-pyrrolidine-2-carboxylic acid N'-(4-methyl-benzenesulfonyl)-hydrazide | M−H 526.0 | 1. Toluene-4-sulfon hydrazide<br>2. 4-Butoxy-benzenesulfonyl chloride | 3,7,2 |
| (2S,4R)-4-Mercapto-1-(2-naphthalen-1-yl-ethylsulfonyl)-pyrrolidine-2-carboxylic acid N'-(4-methyl-benzenesulfonyl)-hydrazide | M−H 526.0 | 1. Toluene-4-sulfon hydrazide<br>2. 2-napthalen-1-yl-ethylsulfonyl chloride | 3,7,2 |
| (2S,4R)-1-(4-Chloro-benzenesulfonyl)-4-mercapto-pyrrolidine-2carboxylic acid N'-(4-methyl-benzenesulfonyl)-hydrazide | M+NH4 507.3 | 1. Toluene-4-sulfon hydrazide<br>2. 4-Chloro-benzenesulfonyl chloride | 3,7,2 |
| (2S,4R)-4-Mercapto-1-(4-trifluoromethyl-bezenesulfonyl)-pyrrolidine-2-carboxylic acid N'-(4-methyl-benzenesulfonyl)-hydrazide | M+NH4 541.4 | 1. Toluene-4-sulfon hydrazide<br>2. 4-trifluoromethyl-benzenesulfonyl chloride | 3,7,2 |
| (2S,4R)-1-(2-Methyl-benzensulfonyl)-4- | M+NH4 487.4 | 1. Toluene-4-sulfon | |

TABLE 1-continued

| Name | Ion Spray MS | Educt | Steps: Scheme 9 |
|---|---|---|---|
| mercapto-pyrrolidine-2-carboxylic acid N'-(4-methyl-benzenesulfonyl)-hydrazide | | hydrazide<br>2. 2-Methyl-benzenesulfonyl chloride | |
| (2S,4R)-1-(2-Naphthalene -1 sulfonyl)-4-mercapto-pyrrolidine-2-carboxylic acid N'-(4-methyl-benzenesulfonyl)-hydrazide | M+NH4 506.3 | 1. Toluene-4-sulfon hydrazide<br>2. Naphthalene-1-sulfonyl chloride | 3,7,2 |
| (2S,4R)-4-Mercapto-1-phenylmethanesulfonyl)-pyrrolidine-2-carboxylic acid N'-(4-methyl-benzenesulfonyl)-hydrazide | M+H 487.4 | 1. Toluene-4-sulfon hydrazide<br>2. Phenylmethanesulfonyl chloride | 3,7,2 |
| (2S,4R)-1-(2,6-Dichloro-benzenesulfonyl)-4-pyrrolidine-2-carboxylic acid N'-(4-methyl-benzenesulfonyl)-hydrazide | M+NH4 541.3 | 1. Toluene-4-sulfon hydrazide<br>2. 2.6-Dichloro-benzenesulfonyl chloride | 3,7,2 |
| (2S,4R)-4-Mercapto-1-(2-trifluoromethyl-benzenesulfonyl)-pyrrolidine-2-carboxylic acid N'-(4-methyl-benzenesulfonyl)-hydrazide | M+NH4 541.4 | 1. Toluene-4-sulfon hydrazide<br>2. 2-trifluoromethyl benzenesulfonyl chloride | 3,7,2 |
| (2S,4R)-1-(3-Methyl-benzensulfonyl)-4-mercapto-pyrrolidine-2-carboxylic acid N'-(4-methyl-benzenesulfonyl)-hydrazide | M+NH4 487.4 | 1. Toluene-4-sulfon hydrazide<br>2. 3-Methyl-benzenesulfonyl chloride | 3,7,2 |
| (2S,4R)-1-(3-Chloro-benzenesulfonyl)-4-mercapto-pyrrolidine-2-carboxylic acid N'-(4-methyl-benzenesulfonyl)-hydrazide | M+NH4 507.3 | 1. Toluene-4-sulfon hydrazide<br>2. 3-Chloro-benzenesulfonyl chloride | 3,7,2 |
| (2S,4R)-1-(2-Chloro-benzenesulfonyl)-4-mercapto-pyrrolidine-2-carboxylic acid N'-(4-methyl-benzenesulfonyl)-hydrazide | M+NH4 507.3 | 1. Toluene-4-sulfon hydrazide<br>2. 2.2-Chloro-benzenesulfonyl chloride | 3,7,2 |
| (2S,4R)-1-(3,4-Dichloro-benzenesulfonyl)-4-mercapto-pyrrolidine-2-carboxylic acid N'-(4-methyl-benzenesulfonyl)-hydrazide | M+NH4 541.3 | 1. Toluene-4-sulfon hydrazide<br>2. 3,4-Dichloro-benzenesulfonyl chloride | 3,7,2 |
| (2S,4R)-4-Mercapto-1-(4-methoxy-benzenesulfonyl)-pyrrolidine-2-carboxylic acid N'-(4-methyl-benzenesulfonyl)-hydrazide | M+NH4 503.4 | 1. Toluene-4-sulfon hydrazide<br>2. 4-methoxy-benzenesulfonyl chloride | 3,7,2 |
| (2S,4R)-4-Mercapto-1-(3-trifluoromethyl-benzenesulfonyl)-pyrrolidine-2-carboxylic acid N'-(4-methyl-benzenesulfonyl)-hydrazide | M+NH4 541.3 | 1. Toluene-4-sulfon hydrazide<br>2. 3-trifluoromethyl benzenesulfonyl chloride | 3,7,2 |
| (2S,4R)-1-Benzsulfonyl-4-mercapto-mercapto-pyrrolidine-2-carboxylic acid N'-(4-methyl-benzenesulfonyl)-hydrazide | M+NH4 473.4 | 1. Toluene-4-sulfon hydrazide<br>2. benzenesulfonyl chloride | 3,7,2 |
| (2S,4R)-1-(3,4-Difluoro-benzenesulfonyl)-4-mercapto-pyrrolidine-2-carboxylic acid N'-(4-methyl-benzenesulfonyl)-hydrazide | M+NH4 509.3 | 1. Toluene-4-sulfon hydrazide<br>2. 3,4-Difluoro-benzenesulfonyl chloride | 3,7,2 |
| (2S,4R)-1-(2,6-Dichloro-benzenesulfonyl)-4-mercapto-pyrrolidine-2-carboxylic acid N'-(4-methyl-benzenesulfonyl)-hydrazide | M+NH4 509.3 | 1. Toluene-4-sulfon hydrazide<br>2. 2,6-Dichloro-benzenesulfonyl chloride | 3,7,2 |
| (2S,4R)-4-Mercapto-1-(2,3,4-trifluoro-benzenesulfonyl)-pyrrolidine-2-carboxylic acid N'-(4-methyl-benzenesulfonyl)-hydrazide | M+NH4 527.3 | 1. Toluene-4-sulfon hydrazide<br>2. 2,3,4-trifluoro-methyl benzenesulfonyl chloride | 3,7,2 |

Example A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
|---|---|
| Gelatine | 150.0 mg |
| Phenol | 4.7 mg |
| Water for injection solutions | ad 1.0 ml |

Example D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single dosages which can be applied individually.

What is claimed is:

1. A compound of formula (I)

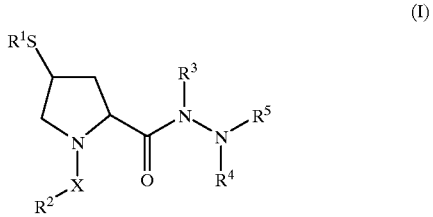

(I)

wherein

R$^1$ is hydrogen, alkylcarbonyl, or arylcarbonyl;

R$^2$ is alkyl, alkylcycloalkyl, alkylcycloalkylalkyl, cycloalkyl, halogenalkyl, carboxyalkyl, aminoalkyl, (mono- and dialkyl)aminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or hetercycylalkyl;

R$^3$ is hydrogen, aryl, alkyl, or arylalkyl, arylsulfonyl, heteroarylsulfonyl;

R$^4$ is hydrogen, arylalkyl, alkyl, aryl, cycloalkyl, cycloalkylalkyl, alkylsulfonyl, arylsulfonyl, arylalkylsulfonyl, heteroarylsulfonyl, carboxyalkyl, carboxyalkylsulfonyl, or alkoxycarbonylalkyl; or the groups —NR$^3$R$^4$ or R$^5$—[N—N(R$^4$)]—R$^3$ form a saturated or unsaturated 5- or 6-membered aliphatic ring;

R$^5$ is hydrogen, alkylsulfonyl, arylsulfonyl, heteroarylsulfonyl, alkoxycarbonyl, aryloxycarbonyl, heteroaryloxycarbonyl, alkylcarbonyl, arylcarbonyl, heteroarylcarbonyl, heteroarylalkylcarbonyl, heterocyclyl, (mono- or di-alkylamino)-alkylcarbonyl, (mono- and dialkyl)aminosulfonyl, arylaminocarbonyl, alkyl, alkylcarbonyl, alkoxycarbonyl, aryl, arylalkyl, arylalkoxycarbonyl, or heteroaryl;

R$^6$ is hydrogen, alkyl, aryl, or carboxyalkyl; X is —S(O)$_2$—, —S(O)$_2$—NH—, —C(O)—, —C(O)NR$^6$ or C(O)—O— or a pharmaceutically acceptable ester, or a pharmaceutically acceptable salt thereof.

2. A compound according to claim 1, wherein R$^1$ is hydrogen.

3. A compound according to claim 2, wherein R$^2$ is alkyl, halogenalkyl, alkylamino, alkoxy, cycloalkyl, cycloalkylamino, aryl, arylalkyl, aryloxy, arylalkylamino, arylalkoxy, heteroaryl, amino, or (mono- and dialkyl)amino.

4. A compound according to claim 3, wherein R$^2$ is alkyl, halogenalkyl, alkylamino, alkoxy, cycloalkyl, cycloalkylamino, aryl, arylalkyl, or heteroaryl.

5. A compound according to claim 4, wherein R$^2$ is aryl or heteroaryl.

6. A compound according to claim 5, wherein R$^2$ is aryl.

7. A compound according to claim 6, wherein R$^2$ is naphthyl or phenyl, wherein phenyl is unsubstituted or substituted by one or more fluor or by one phenyl group.

8. A compound according to claim 7, wherein R$^2$ is naphthyl, 2,3,4,5,6-pentafluorobenzene or biphenyl.

9. A compound according to claim 1, wherein R$^3$ is hydrogen or alkyl.

10. A compound according to claim 9, wherein R$^3$ is hydrogen.

11. A compound according to claim 1, wherein R$^4$ is hydrogen, arylalkyl, alkyl, arylsulfonyl, heteroarylsulfonyl, cycloalkylalkyl, or carboxyalkyl.

12. A compound according to claim 11, wherein R$^4$ is hydrogen, alkyl, arylalkyl, cycloalkyl, arylsulfonyl, or carboxyalkyl.

13. A compound according to claim 12, wherein R$^4$ is hydrogen, alkyl, cycloalkyl, carboxyalkyl or arylalkyl.

14. A compound according to claim 13, wherein R$^4$ is hydrogen, alkyl or arylalkyl.

15. A compound according to claim 14, wherein R$^4$ is hydrogen, 2,4,5-trifluorobenzyl, 2,4-difluorobenzyl, benzyl, methyl, ethyl, isopropyl, isobutyl, benzyl or HO$_2$C—CH$_2$—, or cycloalkylpropylmethyl.

16. A compound according to claim 1, wherein R$^5$ is hydrogen, alkylcarbonyl, alkoxycarbonyl, alkylsulfonyl, aryl, arylalkyl, arylcarbonyl, (mono- and dialkylamino) alkylcarbonyl, (mono- and dialkyl)aminosulfonyl, arylalkoxycarbonyl, arylaminocarbonyl, arylsulfonyl, heteroarylcarbonyl, heteroarylalkylcarbonyl, heteroarylsulfonyl, arylaminocarbonyl, heteroaryl, or heterocyclyl.

17. A compound according to claim 16, wherein R$^5$ is aryl, arylalkyl, arylcarbonyl, arylalkoxy, arylaminocarbonyl, arylsulfonyl, heteroarylcarbonyl, heteroarylalkylcarbonyl, heteroarylsulfonyl, arylaminocarbonyl, heteroaryl, or heterocyclyl.

18. A compound according to claim 17, wherein R$^5$ is arylsulfonyl, arylalkyl, heteroarylalkylcarbonyl, heteroarylsulfonyl.

19. A compound according to claim 18, wherein R$^5$ is 4-methyl-benzenesulfoonyl, benzyl, 4-methoxybenzenesulfonyl, (1H-indol-3-yl)acetyl, thophene-2-yl, or 3,5-dimethyl-isoxyzol-4-sulfonyl.

20. A compound according to claim 1, wherein X is —SO$_2$—, —C(O)—.

21. A compound according to claim 1, wherein X is —SO$_2$—.

22. A compound according to claim 1 having the formula

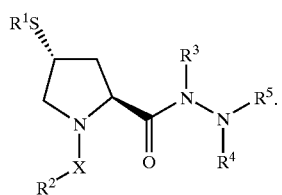

(II)

23. A compound according to claim 22, wherein
R¹ is hydrogen
R² is naphthyl or phenyl, wherein phenyl is optionally substituted by one or more fluor or by one phenyl group;
R³ is hydrogen or alkyl
R⁴ is hydrogen, alkyl or arylalkyl;
R⁵ is arylsulfonyl, arylalkyl, heteroarylalkylcarbonyl, heteroarylsulfonyl; and
X is —SO₂—.

24. A compound according to claim 23, (2S,4R)-4-Mercapto-1-(naphthalene-2-sulfonyl)-pyrrolidine-2-carboxylic acid N'-isobutyl-N'-(4-methyl-benzenesulfonyl)-hydrazide.

25. A compound according to claim 23, (2S,4R)-4-Mercapto-1-(naphthalene-2-sulfonyl) -pyrrolidine-2-carboxylic acid N'-(4-methyl-benzenesulfonyl)-hydrazide.

26. A compound according to claim 23, (2S,4R)/4-Mercapto-1-(naphthalene-2-sulfonyl) -pyrrolidine-2-carboxylic acid N'-benzyl-hydrazide.

27. A compound according to claim 23, (2S,4R)-4-Mercapto-1-(naphthalene-2-sulfonyl) -pyrrolidine-2-carboxylic acid N'-benzyl-N'-(4-methyl-phenylsulfonyl)-hydrazide.

28. A compound according to claim 23, (2S,4R)-4-Mercapto-1-(naphthalene-2-sulfonyl) -pyrrolidine-2-carboxylic acid N'-methyl-N'-(4-methyl-benzenesulfonyl)-hydrazide.

29. A compound according to claim 23, (2S,4R)-4-Mercapto-1-(naphthalene-2-sulfonyl)-pyrrolidine-2-carboxylic acid N'-benzenesulfonyl-hydrazide.A compound according to claim 23, (2S,4R)-4-Mercapto-1-(naphthalene-2-sulfonyl)-pyrrolidine-2-carboxylic acid N'-(4-methoxy-benzenesulfonyl)-hydrazide.

30. A compound according to claim 23, (2S,4R)-4-Mercapto-1-(naphthalene-2-sulfonyl) -pyrrolidine-2-carboxylic acid N'-[(1H-indol-3-yl)-acetyl]-hydrazide.

31. A compound according to claim 23, (2S,4R)-4-Mercapto-1-(naphthalene-2-sulfonyl) -pyrrolidine-2-carboxylic acid N'-thiophene-2-sulfonyl-hydrazide.

32. A compound according to claim 23, (2S,4R)-4-Mercapto-1-(naphthalene-2-sulfonyl) -pyrrolidine-2-carboxylic acid N'-(3,5-dimethyl isoxazole-4-sulfonyl)-hydrazide.

33. A compound according to claim 23, (2S,4R)-4-Mercapto-1-(naphthalene-2-sulfonyl) -pyrrolidine-2-carboxylic acid N'-cyclopropylmethyl-N'-(4-methyl-benzenesulfonyl) -hydrazide.

34. A compound according to claim 23, (2S,4R)-4-Mercapto-1-(naphthalene-2-sulfonyl) -pyrrolidine-2-carboxylic acid N'-(4-methyl-benzenesulfonyl)-N'-(2,4,5-trifluoro-benzyl) -hydrazide.

35. A compound according to claim 23, (2S,4R)-4-Mercapto-1-(naphthalene-2-sulfonyl) -pyrrolidine-2-carboxylic acid N'-(2,5-difluoro-benzyl)-N'-(4-methyl-benzenesulfonyl) -hydrazide.

36. A compound according to claim 23, (2S,4R)-4-Mercapto-1-(naphthalene-2-sulfonyl) -pyrrolidine-2-carboxylic acid N'-isopropyl-N'-(4-methyl-benzensulfonyl)-hydrazide.

37. A compound according to claim 23, (2S,4R)-[N'-[4-Mercapto-1-(naphthalene-2-sulfonyl)-pyrrolidine-2-carbonyl]-N-(4-methyl-benzensulfonyl)-hydrazino]-acetic acid.

38. A compound according to claim 23, (2S,4R)-1-(Biphenyl-4-sulfonyl)-4-mercapto -pyrrolidine-2-carboxylic acid N'-methyl-N'-(4-methyl-benzenesulfonyl)-hydrazide.

39. A compound according to claim 23, (2S,4R)-4-Mercapto-1-(2,3,4,5,6-pentafluoro -benzenesulfonyl)-pyrrolidine-2-carboxylic acid N'-(4-methyl-benzenesulfonyl)-hydrazide.

40. A compound according to claim 23, (2S,4R)-4-Mercapto-1-(naphthalene-2-sulfonyl) -pyrrolidine-2-carboxylic acid N'-benzyl-N'-(4-methoxy-benzenesulfonyl)-hydrazide.

41. A compound according to claim 23, (2S,4R)-4-Mercapto-1-(naphthalene-2-sulfonyl) -pyrrolidine-2-carboxylic acid N-methyl-N'-(4-methyl-benzenesulfonyl)-hydrazide.43.

42. A compound according to claim 23, (2S,4R)-4-Mercapto-1-(naphthalene-2-sulfonyl) -pyrrolidine-2-carboxylic acid N-methyl-N'-benzyl-N'-(4-methyl-benzenesulfonyl) -hydrazide.

* * * * *